(12) United States Patent
Han et al.

(10) Patent No.: US 9,884,877 B2
(45) Date of Patent: Feb. 6, 2018

(54) COMPOUND AND ORGANIC PHOTOELECTRONIC DEVICE AND IMAGE SENSOR

(71) Applicant: Samsung Electronics Co., Ltd., Suwon-Si, Gyeonggi-Do (KR)

(72) Inventors: Moon Gyu Han, Yongin-si (KR); Seon-Jeong Lim, Yongin-si (KR); Takkyun Ro, Hwaseong-si (KR); Kwang Hee Lee, Yongin-si (KR); Dong-Seok Leem, Hwaseong-si (KR); Yong Wan Jin, Seoul (KR); Kyung Bae Park, Hwaseong-si (KR); Sung Young Yun, Suwon-si (KR); Gae Hwang Lee, Seongnam-si (KR); Chul Joon Heo, Busan (KR)

(73) Assignee: SAMSUNG ELECTRONICS CO., LTD., Gyeonggi-Do (KR)

(*) Notice: Subject to any disclaimer, the term of this patent is extended or adjusted under 35 U.S.C. 154(b) by 373 days.

(21) Appl. No.: 14/491,276

(22) Filed: Sep. 19, 2014

(65) Prior Publication Data

US 2015/0303378 A1 Oct. 22, 2015

(30) Foreign Application Priority Data

Apr. 17, 2014 (KR) .................. 10-2014-0046266

(51) Int. Cl.
| | | |
|---|---|---|
| *C07F 5/02* | (2006.01) | |
| *H01L 51/00* | (2006.01) | |
| *H01L 27/30* | (2006.01) | |
| *H01L 51/42* | (2006.01) | |

(52) U.S. Cl.
CPC ............ *C07F 5/022* (2013.01); *H01L 27/307* (2013.01); *H01L 51/008* (2013.01); *H01L 51/0071* (2013.01); *H01L 51/0053* (2013.01); *H01L 51/0069* (2013.01); *H01L 51/4253* (2013.01)

(58) Field of Classification Search
CPC ..................................................... C07F 5/022
See application file for complete search history.

(56) References Cited

U.S. PATENT DOCUMENTS

| | | | | |
|---|---|---|---|---|
| 5,446,157 A | * | 8/1995 | Morgan | ................ A61K 31/69 |
| | | | | 546/13 |
| 6,996,841 B2 | | 2/2006 | Scott et al. | |
| 7,511,811 B2 | | 3/2009 | Scott et al. | |
| 8,089,628 B2 | | 1/2012 | Scott et al. | |
| 2011/0272681 A1 | † | 11/2011 | Sugimoto | |
| 2014/0097416 A1 | † | 4/2014 | Lee | |
| 2014/0117321 A1 | | 5/2014 | Lim et al. | |
| 2015/0303377 A1 | * | 10/2015 | Thompson | .......... C09B 23/0008 |
| | | | | 548/402 |

FOREIGN PATENT DOCUMENTS

| | | | |
|---|---|---|---|
| JP | 2004-200162 A | | 7/2004 |
| JP | 2004200162 A | † | 7/2004 |
| KR | 2009-0119848 A | | 11/2009 |
| KR | 20090119848 A | † | 11/2009 |
| WO | WO-03021212 A1 | | 3/2003 |

OTHER PUBLICATIONS

Wagner et al. "Boron-dipyrromethene dyes for incorporation in synthetic multipigment light-harvesting arrays." Pure and Applied Chemistry, 1996, vol. 68, No. 7, pp. 1373-1380.*
Veldman et al. "The Energy of Charge-Transfer States in Electron Donor—Acceptor Blends: Insight into the Energy Losses in Organic Solar Cells" Advanced Functional Materials, 2009, vol. 19, No. 12, pp. 1939-1948.*
Zhao et al. "Pyridone fused boron-dipyrromethenes: synthesis and properties" Organic & Biomolecular Chemistry, 2013, vol. 11, pp. 372-377.*
C. Zhao et al. "Pyridone fused boron-dipyrromethenes: synthesis and proerties" Organic & Biomolecular Chemistry, 2013, 11, p. 372-377.
M. Mao et al. "New 2,6-modified BODIPY sensitizers for dye-sensitized solar cells" Dyes and Pigments 94 (2012) p. 224-232.

* cited by examiner
† cited by third party

*Primary Examiner* — Joseph R Kosack
(74) *Attorney, Agent, or Firm* — Harness, Dickey & Pierce, PLC

(57) ABSTRACT

A compound may be represented by Chemical Formula 1, an organic photoelectronic device may include a first electrode and a second electrode facing each other with an active layer that includes the compound represented by Chemical Formula 1 between the first electrode and the second electrode, and an image sensor may include the organic photoelectronic device.

3 Claims, 13 Drawing Sheets

COMPOUND AND ORGANIC PHOTOELECTRONIC DEVICE AND IMAGE SENSOR

CROSS REFERENCE TO RELATED APPLICATION

This application claims priority to and the benefit of Korean Patent Application No. 10-2014-0046266 filed in the Korean Intellectual Property Office on Apr. 17, 2014, the entire contents of which are incorporated herein by reference.

BACKGROUND

1. Field

Example embodiments relate to a compound, an organic photoelectronic device, and an image sensor including the same.

2. Description of the Related Art

A photoelectronic device converts light into an electrical signal using photoelectronic effects. The photoelectronic device may include a photodiode and a phototransistor, and may be applied to an image sensor.

An image sensor including a photodiode requires relatively high resolution and thus a relatively small pixel. At present, a silicon photodiode is widely used, but has a problem of deteriorated sensitivity because the silicon photodiode has a relatively small absorption area due to relatively small pixels. Accordingly, an organic material that is capable of replacing silicon has been researched.

The organic material has a relatively high extinction coefficient and selectively absorbs light in a particular wavelength region depending on a molecular structure, and thus may simultaneously replace a photodiode and a color filter and resultantly improve sensitivity and contribute to relatively high integration.

SUMMARY

Example embodiments provide a compound being selectively capable of absorbing light in a green wavelength region.

Example embodiments also provide an organic photoelectronic device that selectively absorbs light in a green wavelength region and improves efficiency.

Example embodiments also provide an image sensor including the organic photoelectronic device.

According to example embodiments, a compound may be represented by the following Chemical Formula 1.

[Chemical Formula 1]

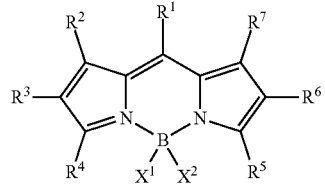

In the above Chemical Formula 1, $R^1$ is one of a substituted or unsubstituted $C_1$ to $C_{30}$ alkyl group, a substituted or unsubstituted $C_3$ to $C_{30}$ cycloalkyl group, a substituted or unsubstituted $C_2$ to $C_{30}$ heterocycloalkyl group, a substituted or unsubstituted $C_6$ to $C_{30}$ aryl group, a substituted or unsubstituted $C_3$ to $C_{30}$ heteroaryl group, a substituted or unsubstituted $C_6$ to $C_{30}$ arylamine group, an amine group, a halogen, a hydroxy group, a cyano group, a cyanovinyl group, a dicyanovinyl group, and a combination thereof, each of $R^2$ to $R^7$ are independently present or two adjacent groups of $R^2$ to $R^7$ are linked to each other to form a fused ring, and are one of hydrogen, a substituted or unsubstituted $C_1$ to $C_{30}$ alkyl group, a substituted or unsubstituted $C_3$ to $C_{30}$ cycloalkyl group, a substituted or unsubstituted $C_2$ to $C_{30}$ heterocycloalkyl group, a substituted or unsubstituted $C_6$ to $C_{30}$ aryl group, a substituted or unsubstituted $C_3$ to $C_{30}$ heteroaryl group, a substituted or unsubstituted $C_1$ to $C_{30}$ carbonyl group, a substituted or unsubstituted $C_6$ to $C_{30}$ arylamine group, an amine group, a halogen, a hydroxy group, a cyano group, a cyanovinyl group, a dicyanovinyl group, and a combination thereof, and each of $X^1$ and $X^2$ are independently one of a halogen, a halogen-containing group, and a combination thereof.

The compound may have a maximum absorption wavelength ($\lambda_{max}$) of about 500 nm to about 600 nm.

The compound may have a HOMO level of about 4.3 to about 7.0 eV and an energy bandgap of about 1.9 to about 3.1 eV.

In the above Chemical Formula 1, each of $X^1$ and $X^2$ may independently be fluorine, and $R^1$ may independently be one of a substituted or unsubstituted $C_6$ to $C_{30}$ aryl group, a cyano group, and a combination thereof.

The compound may be a compound represented by one of the following Chemical Formulae 1a to 1n.

[Chemical Formula 1a]

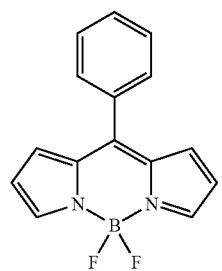

[Chemical Formula 1b]

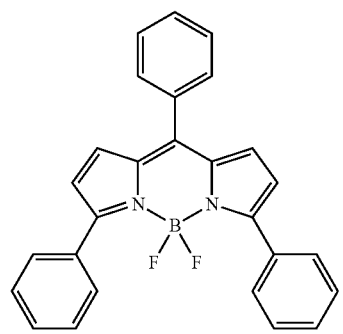

-continued
[Chemical Formula 1c]
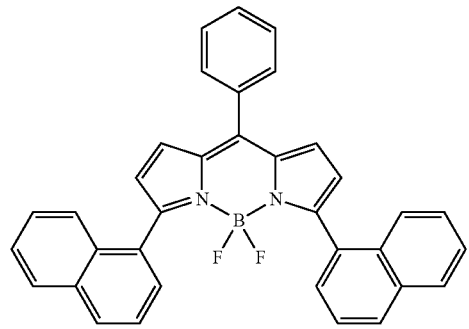
[Chemical Formula 1d]
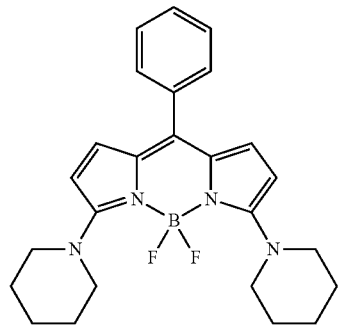
[Chemical Formula 1e]
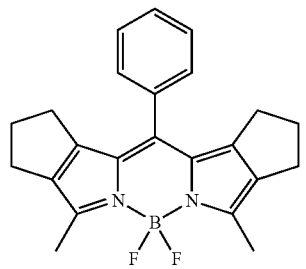
[Chemical Formula 1f]
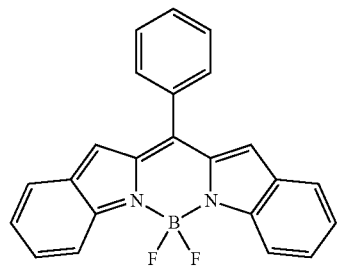
[Chemical Formula 1g]
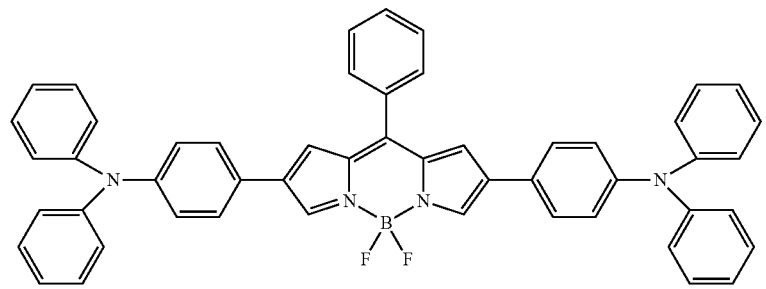
[Chemical Formula 1h]
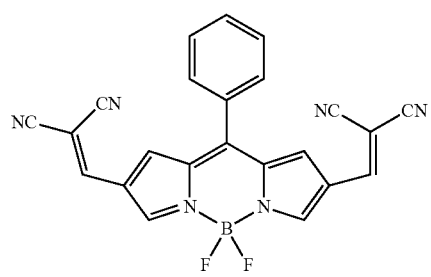
[Chemical Formula 1i]
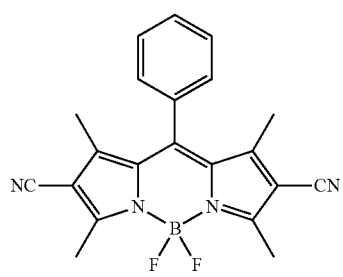
[Chemical Formula 1j]
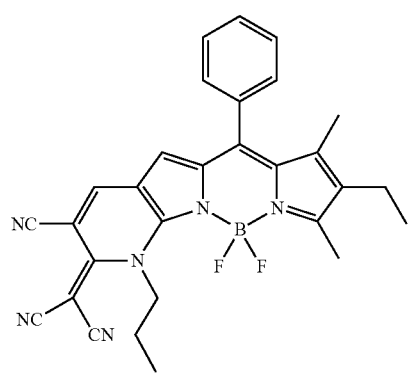
[Chemical Formula 1k]
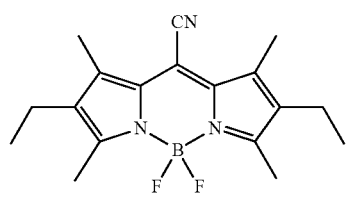

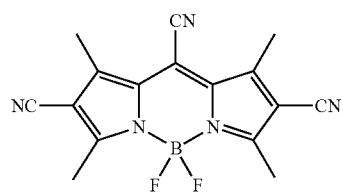

[Chemical Formula 1l]

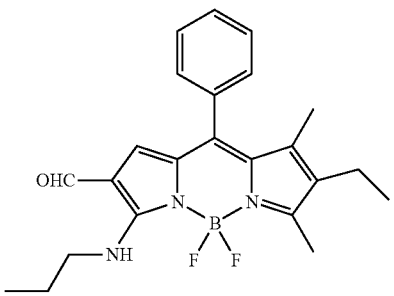

[Chemical Formula 1m]

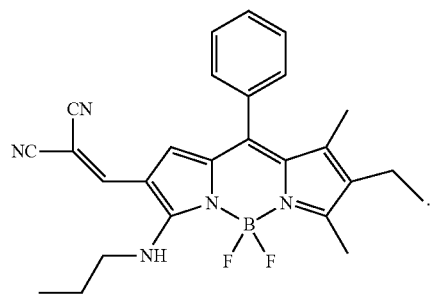

[Chemical Formula 1n]

According to example embodiments, a thin film may include the compound of example embodiments.

The thin film may show an absorbance curve having full width at half maximum (FWHM) of about 50 nm to about 150 nm.

According to example embodiments, an organic photoelectronic device may include a first electrode and a second electrode facing each other, and an active layer between the first electrode and the second electrode, the active layer including a compound represented by the following Chemical Formula 1.

[Chemical Formula 1]

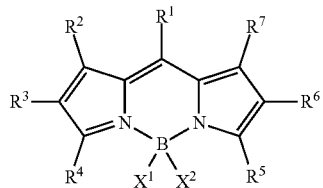

In the above Chemical Formula 1, $R^1$ is one of a substituted or unsubstituted $C_1$ to $C_{30}$ alkyl group, a substituted or unsubstituted $C_3$ to $C_{30}$ cycloalkyl group, a substituted or unsubstituted $C_2$ to $C_{30}$ heterocycloalkyl group, a substituted or unsubstituted $C_6$ to $C_{30}$ aryl group, a substituted or unsubstituted $C_3$ to $C_{30}$ heteroaryl group, a substituted or unsubstituted $C_1$ to $C_{30}$ acyl group, a substituted or unsubstituted $C_6$ to $C_{30}$ arylamine group, an amine group, a halogen, a hydroxy group, a cyano group, a cyanovinyl group, a dicyanovinyl group, and a combination thereof, each of $R^2$ to $R^7$ are independently present or two adjacent groups of $R^2$ to $R^7$ are linked to each other to form a fused ring, and are one of hydrogen, a substituted or unsubstituted $C_1$ to $C_{30}$ alkyl group, a substituted or unsubstituted $C_1$ to $C_{30}$ alkenyl group, a substituted or unsubstituted $C_3$ to $C_{30}$ cycloalkyl group, a substituted or unsubstituted $C_3$ to $C_{30}$ cycloalkenyl group, a substituted or unsubstituted $C_2$ to $C_{30}$ heterocycloalkyl group, a substituted or unsubstituted $C_3$ to $C_{30}$ heterocycloalkenyl group, a substituted or unsubstituted $C_6$ to $C_{30}$ aryl group, a substituted or unsubstituted $C_3$ to $C_{30}$ heteroaryl group, a substituted or unsubstituted $C_1$ to $C_{30}$ acyl group, a substituted or unsubstituted $C_1$ to $C_{30}$ carbonyl group, a substituted or unsubstituted $C_6$ to $C_{30}$ arylamine group, an amine group, a halogen, a hydroxy group, a cyano group, a cyanovinyl group, a dicyanovinyl group, and a combination thereof, and each of $X^1$ and $X^2$ are independently one of a halogen, a halogen-containing group, and a combination thereof.

The compound may have a maximum absorption wavelength ($\lambda_{max}$) of about 500 nm to about 600 nm.

The active layer may show an absorbance curve having a full width at half maximum (FWHM) of about 50 nm to about 150 nm.

The compound may have a HOMO level of about 4.3 to about 7.0 eV and an energy bandgap of about 1.9 to about 3.1 eV.

In the above Chemical Formula 1, each of $X^1$ and $X^2$ may independently be fluorine, and $R^1$ may be one of a substituted or unsubstituted $C_6$ to $C_{30}$ aryl group, a cyano group, and a combination thereof.

The compound represented by the above Chemical Formula 1 may be represented by one of the following Chemical Formulae 1a to 1p.

[Chemical Formula 1a]

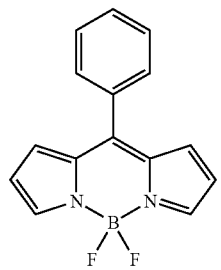

[Chemical Formula 1b]
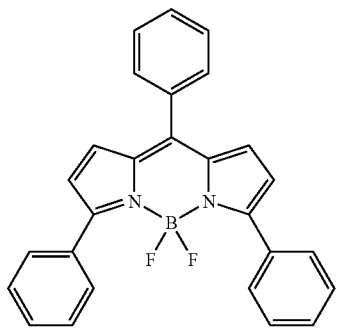
[Chemical Formula 1c]
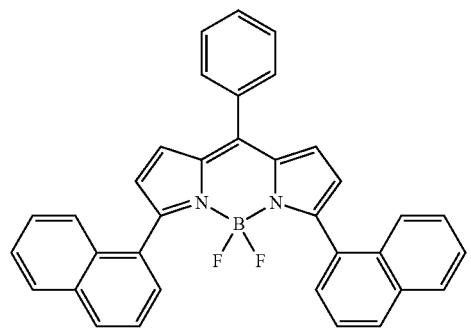
[Chemical Formula 1d]
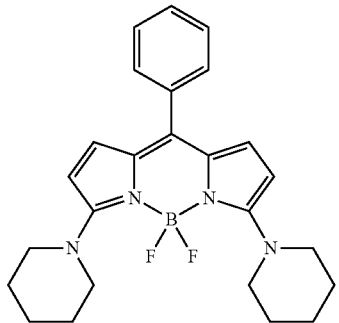
[Chemical Formula 1e]
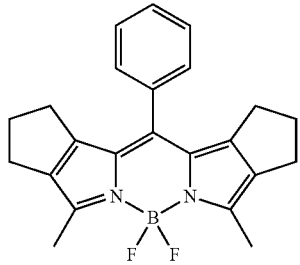
[Chemical Formula 1f]
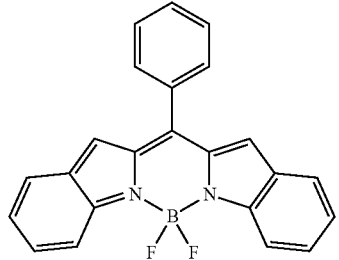
[Chemical Formula 1g]
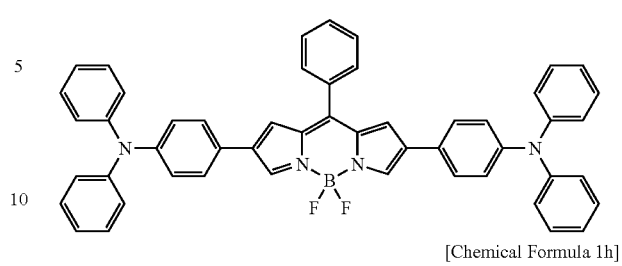
[Chemical Formula 1h]
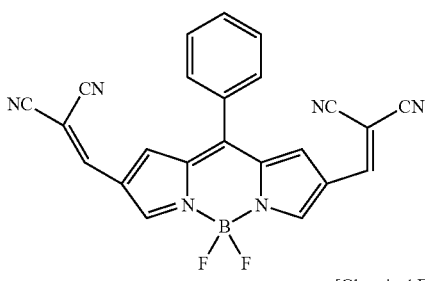
[Chemical Formula 1i]
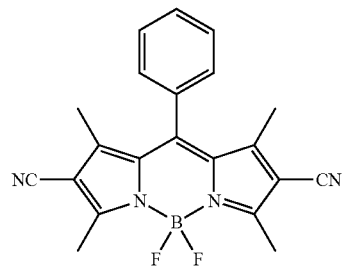
[Chemical Formula 1j]
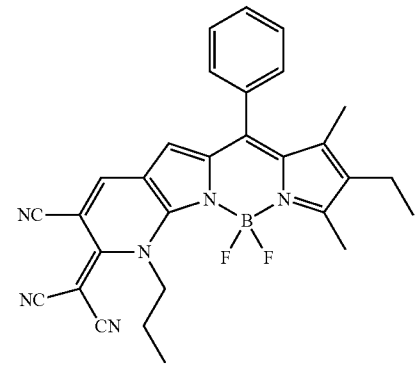
[Chemical Formula 1k]
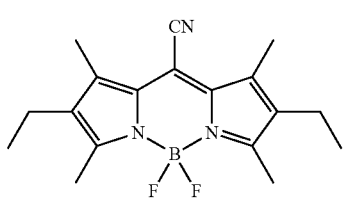
[Chemical Formula 1l]
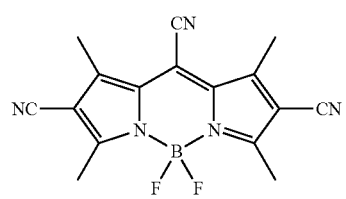

[Chemical Formula 1m]

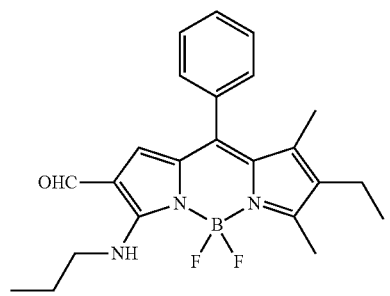

[Chemical Formula 1n]

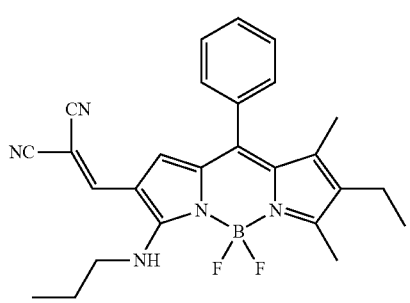

[Chemical Formula 1o]

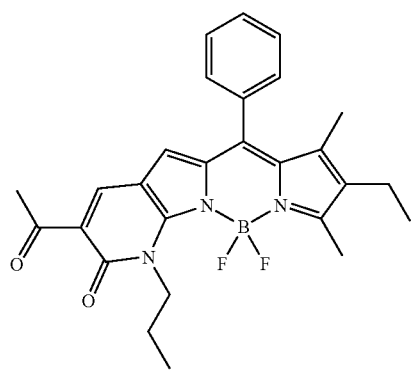

[Chemical Formula 1p]

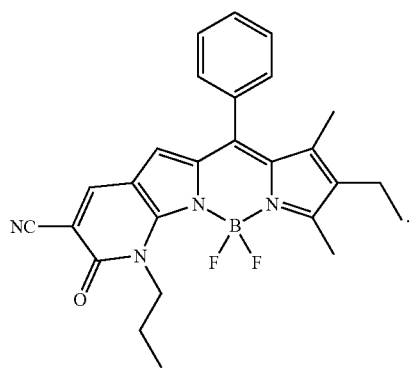

The active layer may further include one of a p-type semiconductor compound and an n-type semiconductor compound.

The p-type semiconductor compound may include at least one of a compound represented by the following Chemical Formula 2 and a compound represented by the following Chemical Formula 3.

[Chemical Formula 2]

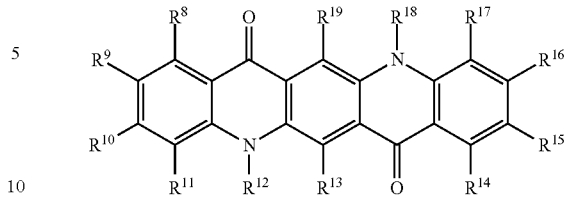

In the above Chemical Formula 2, each of $R^8$ to $R^{19}$ are independently one of hydrogen, a substituted or unsubstituted $C_1$ to $C_{30}$ alkyl group, a substituted or unsubstituted $C_3$ to $C_{30}$ cycloalkyl group, a substituted or unsubstituted $C_2$ to $C_{30}$ heterocycloalkyl group, a substituted or unsubstituted $C_6$ to $C_{30}$ aryl group, a substituted or unsubstituted $C_3$ to $C_{30}$ heteroaryl group, a substituted or unsubstituted $C_1$ to $C_{30}$ alkoxy group, a halogen, and a combination thereof,

[Chemical Formula 3]

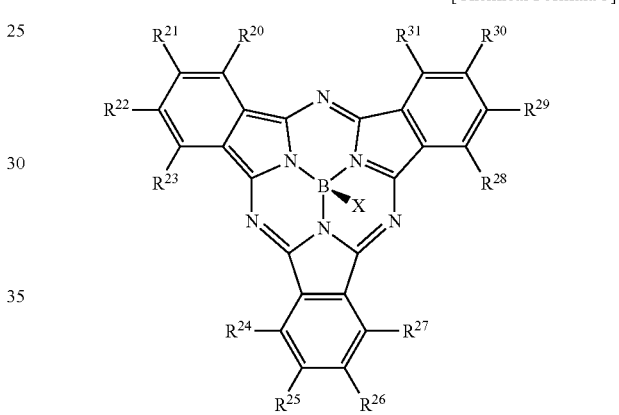

In the above Chemical Formula 3, each of $R^{20}$ to $R^{31}$ are independently one of hydrogen, a substituted or unsubstituted $C_1$ to $C_{30}$ alkyl group, a substituted or unsubstituted $C_6$ to $C_{30}$ aryl group, a substituted or unsubstituted $C_3$ to $C_{30}$ heteroaryl group, a halogen, a halogen-containing group, and a combination thereof, and X is an anion.

The active layer may selectively absorb light in a green wavelength region.

The active layer may include an intrinsic layer having a first side and a second side including the compound represented by the above Chemical Formula 1.

The active layer may further include at least one of a p-type layer on the first side of the intrinsic layer and an n-type layer on the second side of the intrinsic layer.

According to example embodiments, an image sensor may include the organic photoelectronic device.

The image sensor may include a semiconductor substrate integrated with a plurality of first photo-sensing devices sensing light in a blue wavelength region and a plurality of second photo-sensing devices sensing light in a red wavelength region, a color filter layer on the semiconductor substrate and including a blue filter that selectively absorbs light in the blue wavelength region and a red filter that selectively absorbs light in the red wavelength region, and the organic photoelectronic device on the color filter layer and selectively absorbing light in a green wavelength region.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
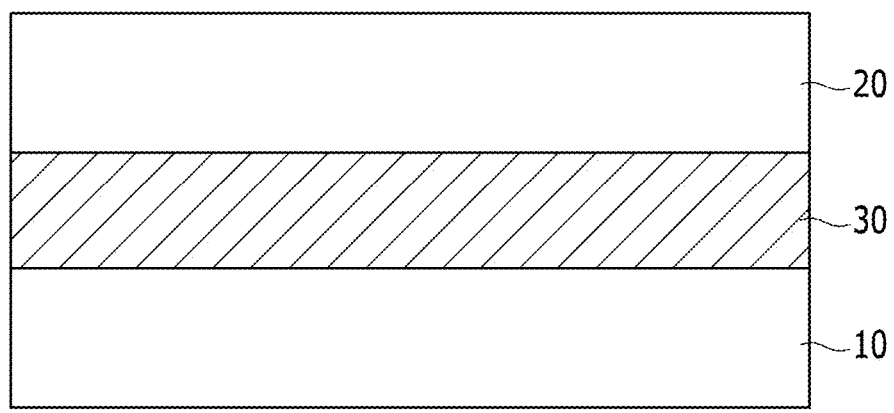
FIG. 1 is a cross-sectional view showing an organic photoelectronic device according to example embodiments.

Example embodiments will hereinafter be described in detail, and may be easily performed by those who have common knowledge in the related art. However, this disclosure may be embodied in many different forms and is not construed as limited to the example embodiments set forth herein.

As used herein, when a definition is not otherwise provided, the term "substituted" refers to one substituted with a substituent selected from a halogen (F, Br, Cl, or I), a hydroxy group, an alkoxy group, a nitro group, a cyano group, an amino group, an azido group, an amidino group, a hydrazino group, a hydrazono group, a carbonyl group, a carbamyl group, a thiol group, an ester group, a carboxyl group or a salt thereof, a sulfonic acid group or a salt thereof, phosphoric acid or a salt thereof, a $C_1$ to $C_{20}$ alkyl group, a $C_2$ to $C_{20}$ alkenyl group, a $C_2$ to $C_{20}$ alkynyl group, a $C_6$ to $C_{30}$ aryl group, a $C_7$ to $C_{30}$ arylalkyl group, a $C_1$ to $C_4$ alkoxy group, a $C_1$ to $C_{20}$ heteroalkyl group, a $C_3$ to $C_{20}$ heteroarylalkyl group, a $C_3$ to $C_{30}$ cycloalkyl group, a $C_3$ to $C_{15}$ cycloalkenyl group, a $C_6$ to $C_{15}$ cycloalkynyl group, a $C_2$ to $C_{20}$ heterocycloalkyl group, and a combination thereof, instead of hydrogen of a compound.

As used herein, when specific definition is not otherwise provided, the term "hetero" refers to one including 1 to 3 heteroatoms selected from N, O, S, and P.

In the drawings, the thickness of layers, films, panels, regions, etc., are exaggerated for clarity. Like reference numerals designate like elements throughout the specification. It will be understood that when an element such as a layer, film, region, or substrate is referred to as being "on" another element, it can be directly on the other element or intervening elements may also be present. In contrast, when an element is referred to as being "directly on" another element, there are no intervening elements present.

In the drawings, parts having no relationship with the description are omitted for clarity of the embodiments, and the same or similar constituent elements are indicated by the same reference numeral throughout the specification.

It should be understood that, although the terms first, second, third, etc. may be used herein to describe various elements, components, regions, layers and/or sections, these elements, components, regions, layers, and/or sections should not be limited by these terms. These terms are only used to distinguish one element, component, region, layer, or section from another region, layer, or section. Thus, a first element, component, region, layer, or section discussed below could be termed a second element, component, region, layer, or section without departing from the teachings of example embodiments.

Spatially relative terms (e.g., "beneath," "below," "lower," "above," "upper," and the like) may be used herein for ease of description to describe one element or feature's relationship to another element(s) or feature(s) as illustrated in the figures. It should be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

The terminology used herein is for the purpose of describing various embodiments only and is not intended to be limiting of example embodiments. As used herein, the singular forms "a," "an," and "the" are intended to include the plural forms as well, unless the context clearly indicates otherwise. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the shapes of regions illustrated herein but are to include deviations in shapes that result, for example, from manufacturing.

Unless otherwise defined, all terms (including technical and scientific terms) used herein have the same meaning as commonly understood by one of ordinary skill in the art to which example embodiments belong. It will be further understood that terms, including those defined in commonly used dictionaries, should be interpreted as having a meaning that is consistent with their meaning in the context of the relevant art and will not be interpreted in an idealized or overly formal sense unless expressly so defined herein.

Hereinafter, a compound according to example embodiments is described.

A compound according to example embodiments is represented by the following Chemical Formula 1.

[Chemical Formula 1]

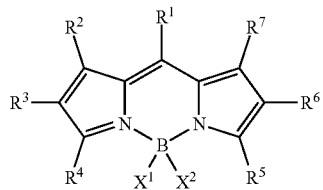

In the above Chemical Formula 1, $R^1$ is one of a substituted or unsubstituted $C_1$ to $C_{30}$ alkyl group, a substituted or unsubstituted $C_3$ to $C_{30}$ cycloalkyl group, a substituted or unsubstituted $C_2$ to $C_{30}$ heterocycloalkyl group, a substituted or unsubstituted $C_6$ to $C_{30}$ aryl group, a substituted or unsubstituted $C_3$ to $C_{30}$ heteroaryl group, a substituted or unsubstituted $C_6$ to $C_{30}$ arylamine group, an amine group, a halogen, a hydroxy group, a cyano group, a cyanovinyl group, a dicyanovinyl group, and a combination thereof, each of $R^2$ to $R^7$ are independently present or two adjacent groups of $R^2$ to $R^7$ are linked to each other to form a fused ring, and are one of hydrogen, a substituted or unsubstituted $C_1$ to $C_{30}$ alkyl group, a substituted or unsubstituted $C_3$ to $C_{30}$ cycloalkyl group, a substituted or unsubstituted $C_2$ to $C_{30}$ heterocycloalkyl group, a substituted or unsubstituted $C_6$ to $C_{30}$ aryl group, a substituted or unsubstituted $C_3$ to $C_{30}$ heteroaryl group, a substituted or unsubstituted $C_1$ to $C_{30}$ carbonyl group, a substituted or unsubstituted $C_6$ to $C_{30}$ arylamine group, an amine group, a halogen, a hydroxy group, a cyano group, a cyanovinyl group, a dicyanovinyl group, and a combination thereof, and each of $X^1$ and $X^2$ are independently one of a halogen, a halogen-containing group, and a combination thereof.

The compound may selectively absorb light in a green wavelength region, and may have a maximum absorption wavelength ($\lambda_{max}$) of about 500 nm to about 600 nm.

The compound may show an absorbance curve having a relatively narrow full width at half maximum (FWHM) of about 50 nm to about 150 nm in a thin film state. Herein, the FWHM is a width of a wavelength corresponding to a half of a maximum absorbance point, and a smaller FWHM indicates selective absorbance of light in a relatively narrow wavelength region and a relatively high wavelength selectivity. Accordingly, a compound having FWHM within the range may have relatively high selectivity for a green wavelength region.

The compound may have a HOMO level of about 4.3 to about 7.0 eV and an energy bandgap of about 1.9 to about 3.1 eV. When the compound has the HOMO level and energy bandgap within the ranges, the compound may be applied as an n-type or p-type semiconductor that selectively absorbs light in a green wavelength region, and thus has relatively high external quantum efficiency (EQE) thereby improving photoelectric conversion efficiency.

For example, in the above Chemical Formula 1, $X^1$ and $X^2$ may independently be fluorine.

For example, in the above Chemical Formula 1, $R^1$ may be one of a substituted or unsubstituted $C_6$ to $C_{30}$ aryl group, a cyano group, and a combination thereof. The aryl group may be, for example, a phenyl group.

The compound represented by the above Chemical Formula 1 may be represented by one of the following Chemical Formulae 1a to 1n, but is not limited thereto.

[Chemical Formula 1a]

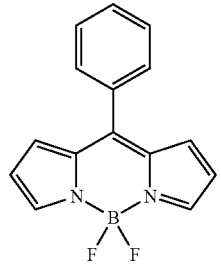

[Chemical Formula 1b]

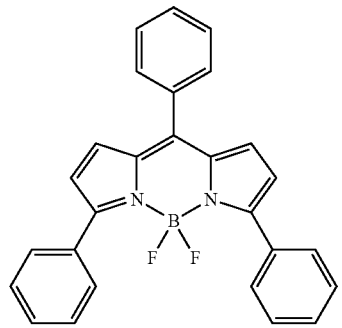

[Chemical Formula 1c]

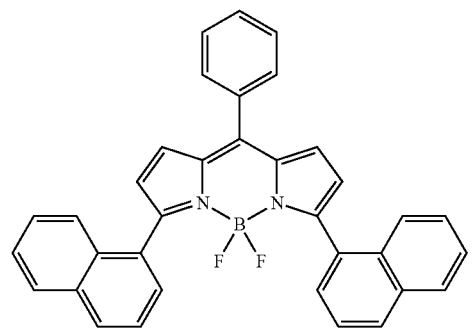

[Chemical Formula 1d]

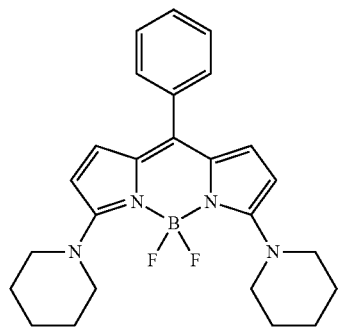

[Chemical Formula 1e]

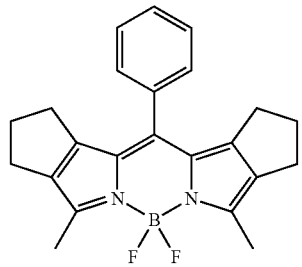

[Chemical Formula 1f]

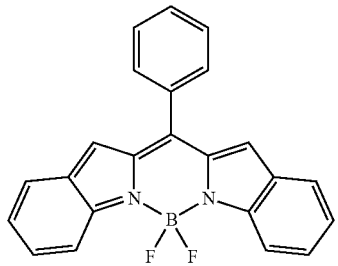

[Chemical Formula 1g]

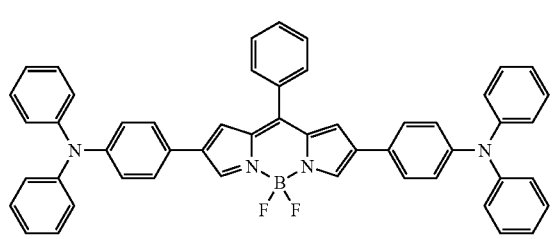

[Chemical Formula 1h]

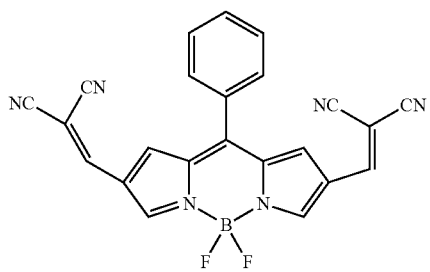

[Chemical Formula 1i]

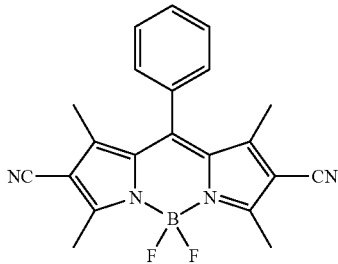

[Chemical Formula 1j]

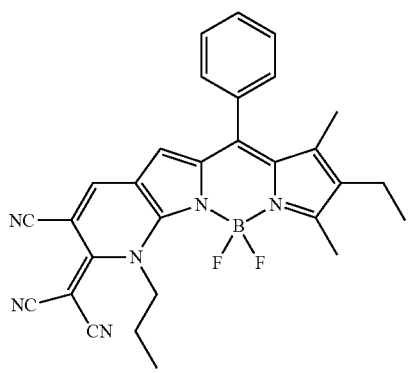

[Chemical Formula 1k]

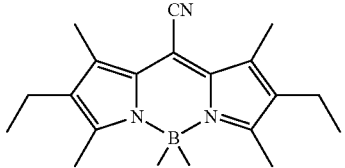

[Chemical Formula 1l]

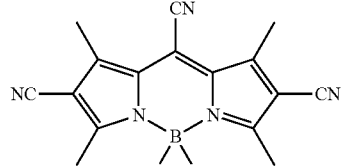

[Chemical Formula 1m]

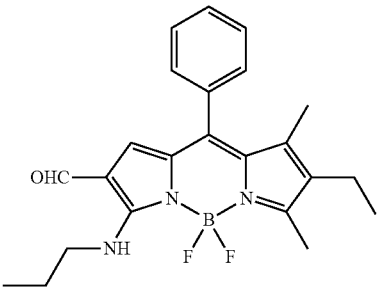

[Chemical Formula 1n]

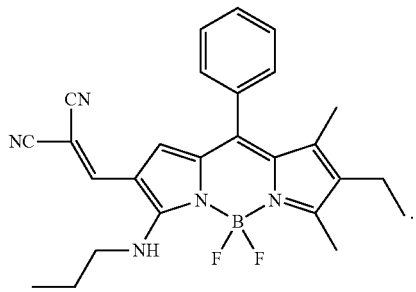

Hereinafter, an organic photoelectronic device including the compound according to example embodiments is described referring to the drawing.

FIG. 1 is a cross-sectional view showing an organic photoelectronic device according to example embodiments.

Referring to FIG. 1, an organic photoelectronic device 100 according to example embodiments includes a first electrode 10 and a second electrode 20 facing each other, and an active layer 30 interposed between the first electrode 10 and the second electrode 20.

One of the first electrode 10 and the second electrode 20 is an anode and the other is cathode. At least one of the first electrode 10 and the second electrode 20 may be a light-transmitting electrode, and the light-transmitting electrode may be made of, for example, a transparent conductor such as indium tin oxide (ITO) or indium zinc oxide (IZO), or a metal thin layer of a thin monolayer or a multilayer. When one of the first electrode 10 and the second electrode 20 is a non-light-transmitting electrode, it may be made of, for example, an opaque conductor such as aluminum (Al).

The active layer 30 includes a p-type semiconductor material and an n-type semiconductor material to form a pn junction, and absorbs light externally to generate excitons and then separates the generated excitons into holes and electrons.

The active layer 30 includes a compound represented by the following Chemical Formula 1.

[Chemical Formula 1]

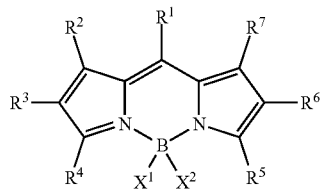

In the above Chemical Formula 1, $R^1$ is one of a substituted or unsubstituted C1 to $C_{30}$ alkyl group, a substituted or unsubstituted C3 to $C_{30}$ cycloalkyl group, a substituted or unsubstituted C2 to $C_{30}$ heterocycloalkyl group, a substituted or unsubstituted C6 to $C_{30}$ aryl group, a substituted or unsubstituted C3 to $C_{30}$ heteroaryl group, a substituted or unsubstituted C1 to $C_{30}$ acyl group, a substituted or unsubstituted C6 to $C_{30}$ arylamine group, an amine group, a halogen, a hydroxy group, a cyano group, a cyanovinyl group, a dicyanovinyl group, and a combination thereof, each of $R^2$ to $R^7$ are independently present or two adjacent groups of $R^2$ to $R^7$ are linked to each other to form a fused ring, and are one of hydrogen, a substituted or unsubstituted C1 to $C_{30}$ alkyl group, a substituted or unsubstituted C1 to $C_{30}$ alkenyl group, a substituted or unsubstituted C3 to $C_{30}$ cycloalkyl group, a substituted or unsubstituted C3 to $C_{30}$ cycloalkenyl group, a substituted or unsubstituted C2 to $C_{30}$ heterocycloalkyl group, a substituted or unsubstituted C3 to $C_{30}$ heterocycloalkenyl group, a substituted or unsubstituted C6 to $C_{30}$ aryl group, a substituted or unsubstituted C3 to $C_{30}$ heteroaryl group, a substituted or unsubstituted C1 to $C_{30}$ acyl group, a substituted or unsubstituted C1 to $C_{30}$ carbonyl group, a substituted or unsubstituted C6 to $C_{30}$ arylamine group, an amine group, a halogen, a hydroxy group, a cyano group, a cyanovinyl group, a dicyanovinyl group, and a combination thereof, and each of $X^1$ and $X^2$ are independently one of a halogen, a halogen-containing group, and a combination thereof.

The compound may selectively absorb light in a green wavelength region, and the active layer 30 including the compound may selectively absorb light in a green wavelength having a maximum absorption wavelength ($\lambda_{max}$) of about 500 nm to about 600 nm.

The active layer 30 may show a relatively narrow absorbance curve having a full width at half maximum (FWHM) of about 50 nm to about 150 nm. Accordingly, the active layer 30 may have relatively high selectivity for light in a green wavelength region.

The compound may have a HOMO level of about 4.3 to about 7.0 eV and an energy bandgap of about 1.9 to about 3.1 eV. When the compound has the HOMO level and the energy bandgap within the ranges, the compound may be applied as an n-type or p-type semiconductor to effectively absorb light in a green wavelength region.

For example, in the above Chemical Formula 1, $X^1$ and $X^2$ may independently be fluorine.

For example, in the above Chemical Formula 1, $R^1$ may be one of a substituted or unsubstituted $C_6$ to $C_{30}$ aryl group, a cyano group, and a combination thereof. The aryl group may be, for example, a phenyl group.

The compound may be, for example, represented by the following Chemical Formulae 1a to 1p, but is not limited thereto.

[Chemical Formula 1a]

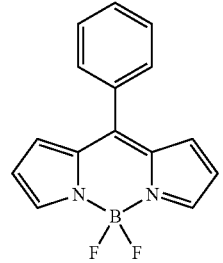

[Chemical Formula 1b]

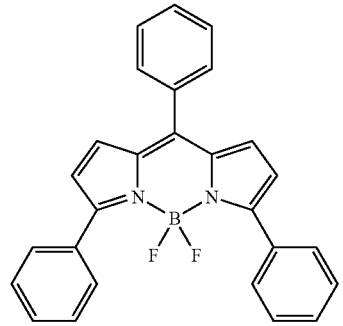

[Chemical Formula 1c]

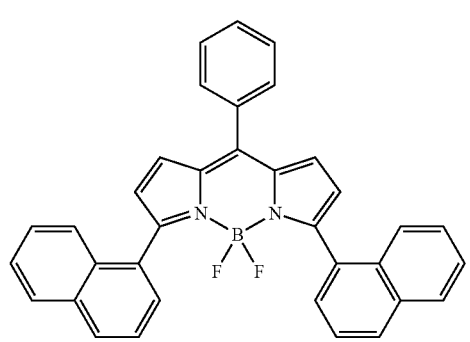

[Chemical Formula 1d]

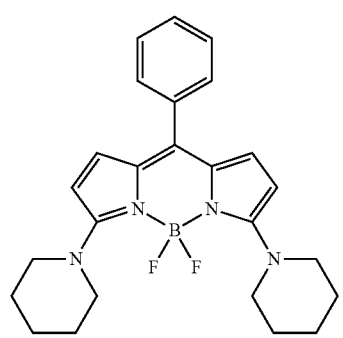

[Chemical Formula 1e]
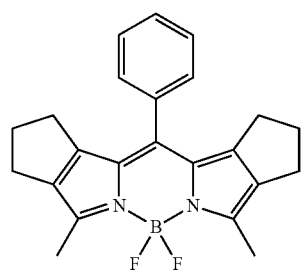
[Chemical Formula 1f]
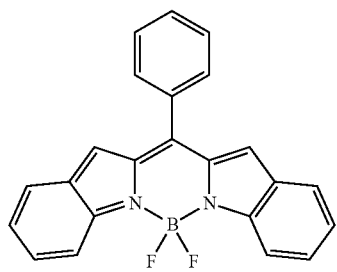
[Chemical Formula 1g]
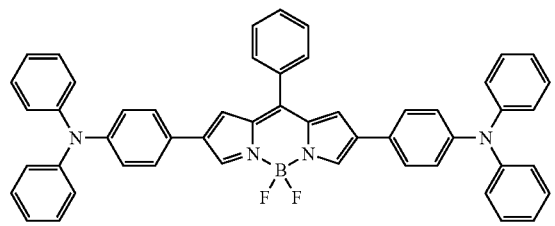
[Chemical Formula 1h]
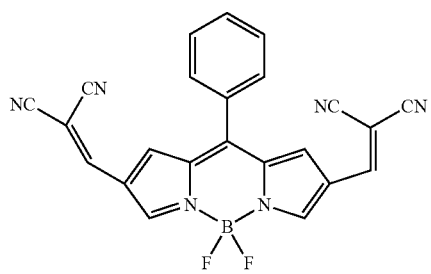
[Chemical Formula 1i]
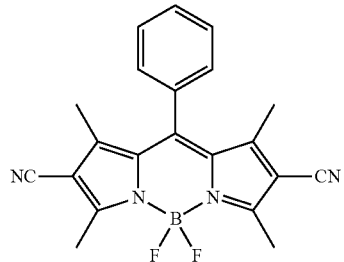
[Chemical Formula 1j]
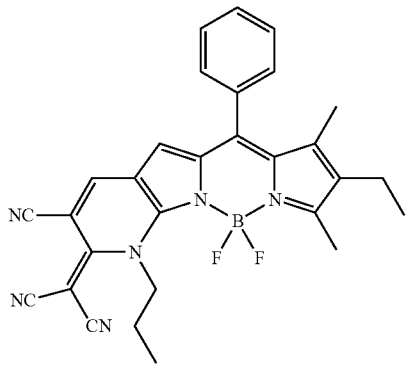
[Chemical Formula 1k]
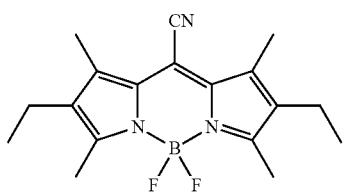
[Chemical Formula 1l]
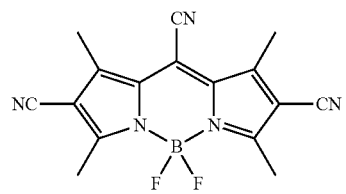
[Chemical Formula 1m]
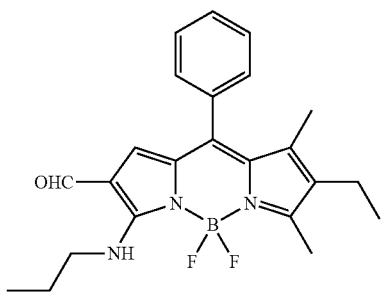
[Chemical Formula 1n]
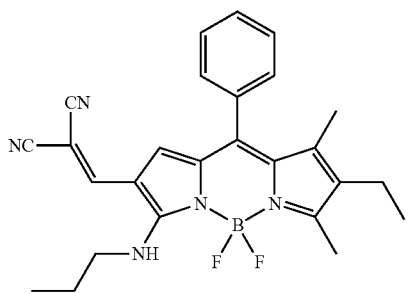

[Chemical Formula 1o]

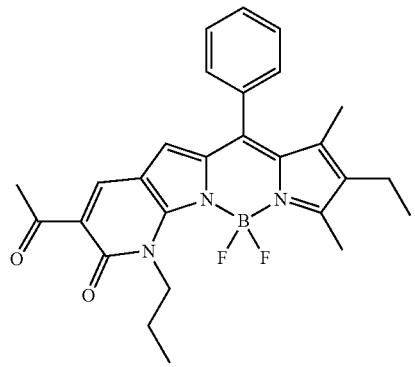

[Chemical Formula 1p]

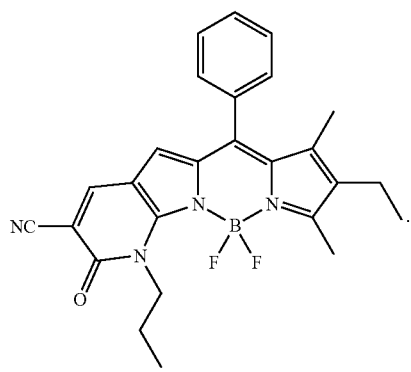

The compound may be applied as an n-type semiconductor or a p-type semiconductor in the active layer 30. When the compound is applied as an n-type semiconductor, a p-type semiconductor may be further included to form a pn junction with the n-type semiconductor, while when the compound is applied as a p-type semiconductor, an n-type semiconductor may be further included to form a pn junction with the p-type semiconductor.

For example, when the compound is an n-type semiconductor, a p-type semiconductor represented by the following Chemical Formula 2 may be further included.

[Chemical Formula 2]

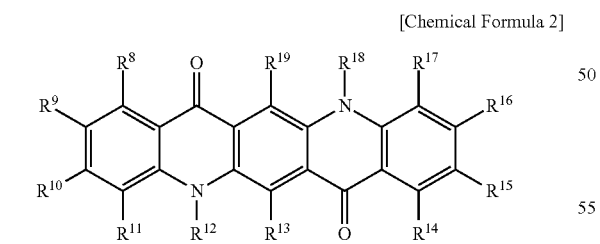

In the above Chemical Formula 2, each of $R^8$ to $R^{19}$ are independently one of hydrogen, a substituted or unsubstituted $C_1$ to $C_{30}$ alkyl group, a substituted or unsubstituted $C_3$ to $C_{30}$ cycloalkyl group, a substituted or unsubstituted $C_2$ to $C_{30}$ heterocycloalkyl group, a substituted or unsubstituted $C_6$ to $C_{30}$ aryl group, a substituted or unsubstituted $C_3$ to $C_{30}$ heteroaryl group, a substituted or unsubstituted $C_1$ to $C_{30}$ alkoxy group, a halogen, and a combination thereof.

The compound represented by the above Chemical Formula 2 may be, for example, at least one of compounds represented by the following Chemical Formulae 2a to 2h, but is not limited thereto.

[Chemical Formula 2a]

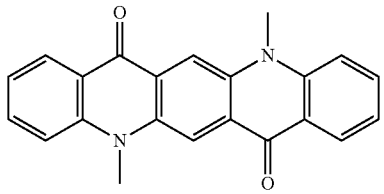

[Chemical Formula 2b]

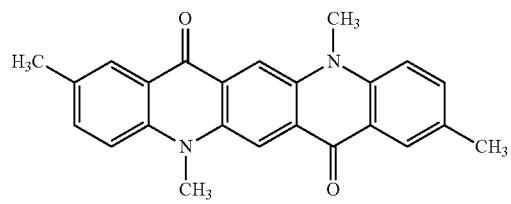

[Chemical Formula 2c]

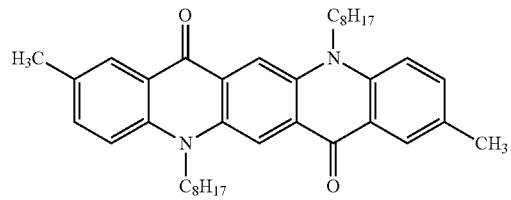

[Chemical Formula 2d]

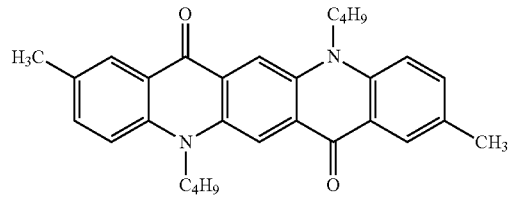

[Chemical Formula 2e]

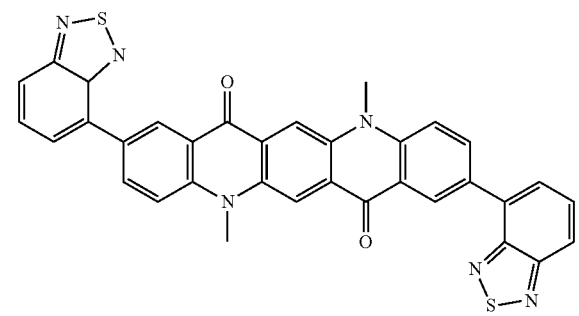

-continued

[Chemical Formula 2f]

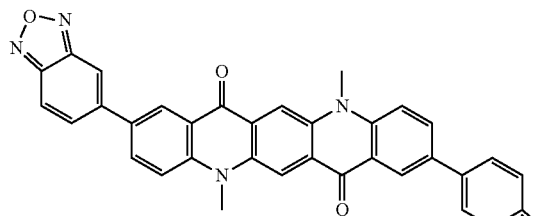

[Chemical Formula 2g]

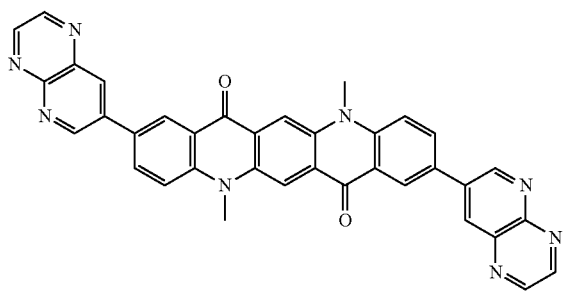

[Chemical Formula 2h]

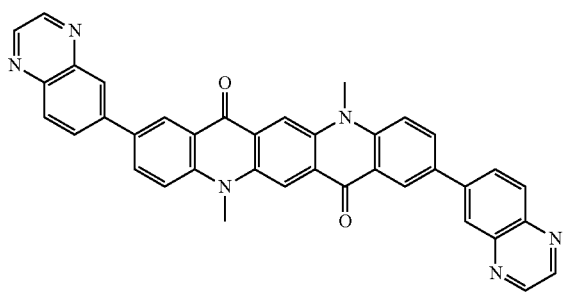

For example, when the compound is an n-type semiconductor, a p-type semiconductor represented by the following Chemical Formula 3 may be further included.

[Chemical Formula 3]

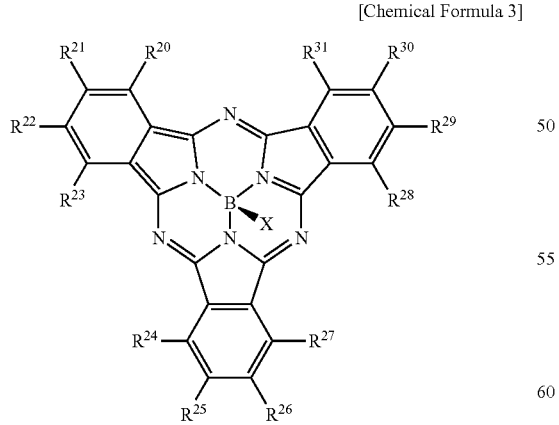

In the above Chemical Formula 3, each of $R^{20}$ to $R^{31}$ are independently one of hydrogen, a substituted or unsubstituted $C_1$ to $C_{30}$ alkyl group, a substituted or unsubstituted $C_6$ to $C_{30}$ aryl group, a substituted or unsubstituted $C_3$ to $C_{30}$ heteroaryl group, a halogen, a halogen-containing group, and a combination thereof, and X is an anion.

The compound represented by the above Chemical Formula 3 may be, for example, at least one of compounds represented by the following Chemical Formulae 3a to 3e, but is not limited thereto.

[Chemical Formula 3a]

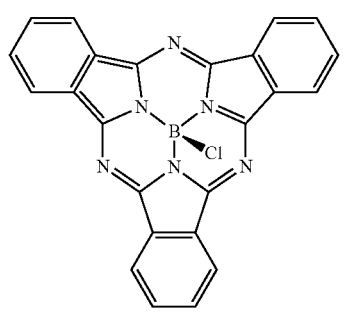

[Chemical Formula 3b]

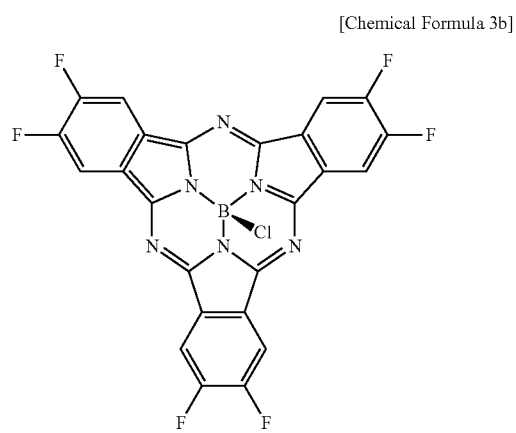

[Chemical Formula 3c]

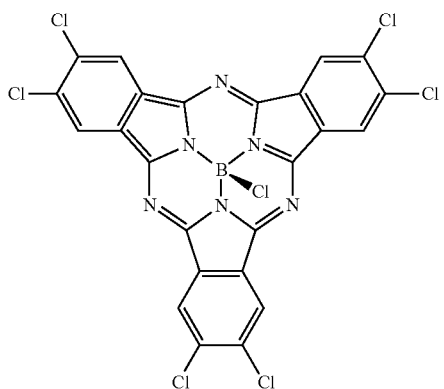

-continued

[Chemical Formula 3d]

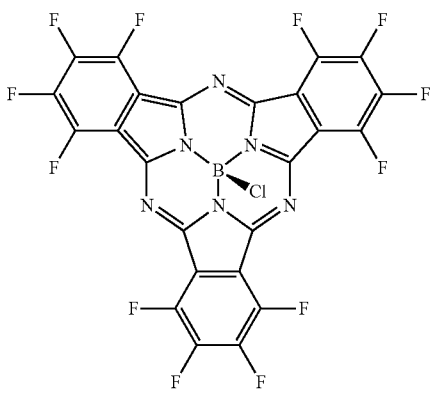

[Chemical Formula 3e]

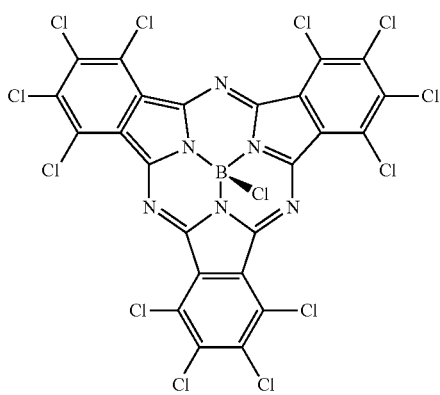

The active layer 30 may be a monolayer or a multilayer. The active layer 30 may be, for example, an intrinsic layer (I layer), a p-type layer/I layer, an I layer/n-type layer, a p-type layer/I layer/n-type layer, and a p-type layer/n-type layer.

The intrinsic layer (I layer) may include the p-type semiconductor compound and the n-type semiconductor compound in a ratio of about 1:100 to about 100:1. The compounds may be included in a ratio ranging from about 1:50 to about 50:1 within the range, specifically, about 1:10 to about 10:1, and more specifically, about 1:about 1. When the p-type and n-type semiconductors have a composition ratio within the range, an exciton may be effectively produced, and a pn junction may be effectively formed.

The p-type layer may include the p-type semiconductor compound, and the n-type layer may include the n-type semiconductor compound.

The active layer 30 may have a thickness of about 1 nm to about 500 nm, and specifically about 5 nm to about 300 nm. When the active layer 30 has a thickness within the range, the active layer may effectively absorb light, effectively separate holes from electrons, and deliver them, thereby effectively improving photoelectric conversion efficiency.

In the organic photoelectronic device 100, when light enters from the first electrode 10 and/or second electrode 20, and when the active layer 30 adsorbs light having a predetermined or given wavelength region, excitons may be produced from inside the organic photoelectronic device 100. The excitons are separated into holes and electrons at the active layer 30, the separated holes are transported to an anode that is one of the first electrode 10 and second electrode 20, and the separated electrons are transported to the cathode that is the other of and the first electrode 10 and second electrode 20, so as to flow a current in the organic photoelectronic device.

Figure 2:
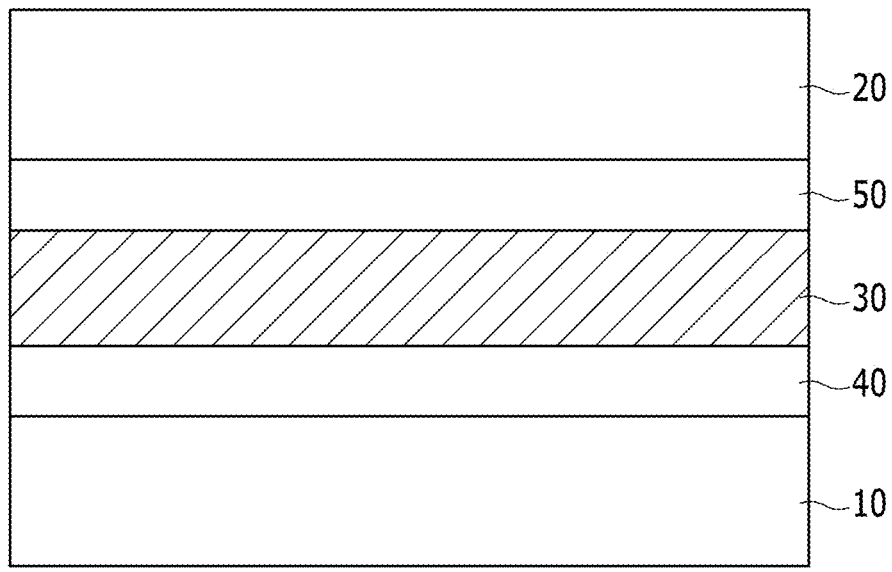
FIG. 2 is a cross-sectional view showing an organic photoelectronic device according to example embodiments.

Referring to FIG. 2, an organic photoelectronic device according to example embodiments is described.

FIG. 2 is a cross-sectional view of an organic photoelectronic device according to example embodiments.

Referring to FIG. 2, an organic photoelectronic device 200 according to example embodiments includes a first electrode 10 and a second electrode 20 facing each other, and an active layer 30 interposed between the first electrode 10 and the second electrode 20 like the example embodiment illustrated in FIG. 1.

However, the organic photoelectronic device 200 according to example embodiments further includes charge auxiliary layers 40 and 50 between the first electrode 10 and the active layer 30, and the second electrode 20 and the active layer 30, respectively, unlike the example embodiment illustrated in FIG. 1. The charge auxiliary layers 40 and 50 may facilitate the transfer of holes and electrons separated from the active layer 30, so as to increase efficiency.

The charge auxiliary layers 40 and 50 may be at least one selected from a hole injection layer (HIL) for facilitating hole injection, a hole transport layer (HTL) for facilitating hole transport, an electron blocking layer (EBL) for preventing or inhibiting electron transport, an electron injection layer (EIL) for facilitating electron injection, an electron transport layer (ETL) for facilitating electron transport, and a hole blocking layer (HBL) for preventing or inhibiting hole transport.

The charge auxiliary layers 40 and 50 may include, for example, an organic material, an inorganic material, or an organic/inorganic material. The organic material may be an organic compound having hole or electron characteristics, and the inorganic material may be, for example, a metal oxide (e.g., molybdenum oxide, tungsten oxide, and nickel oxide).

The hole transport layer (HTL) may include one selected from, for example, poly(3,4-ethylenedioxythiophene):poly(styrenesulfonate) (PEDOT:PSS), polyarylamine, poly(N-vinylcarbazole), polyaniline, polypyrrole, N,N,N',N'-tetrakis(4-methoxyphenyl)-benzidine (TPD), 4-bis[N-(1-naphthyl)-N-phenyl-amino]biphenyl (α-NPD), m-MTDATA, 4,4',4"-tris(N-carbazolyl)-triphenylamine (TCTA), and a combination thereof, but is not limited thereto.

The electron blocking layer (EBL) may include one selected from, for example, poly(3,4-ethylenedioxythiophene):poly(styrenesulfonate) (PEDOT:PSS), polyarylamine, poly(N-vinylcarbazole), polyaniline, polypyrrole, N,N,N',N'-tetrakis(4-methoxyphenyl)-benzidine (TPD), 4-bis[N-(1-naphthyl)-N-phenyl-amino]biphenyl (α-NPD), m-MTDATA, 4,4',4"-tris(N-carbazolyl)-triphenylamine (TCTA), and a combination thereof, but is not limited thereto.

The electron transport layer (ETL) may include one selected from, for example, 1,4,5,8-naphthalene-tetracarboxylic dianhydride (NTCDA), bathocuproine (BCP), LiF, $Alq_3$, $Gaq_3$, $Inq_3$, $Znq_2$, $Zn(BTZ)_2$, $BeBq_2$, and a combination thereof, but is not limited thereto.

The hole blocking layer (HBL) may include one selected from, for example, 1,4,5,8-naphthalene-tetracarboxylic dianhydride (NTCDA), bathocuproine (BCP), LiF, $Alq_3$, $Gaq_3$, $Inq_3$, $Znq_2$, $Zn(BTZ)_2$, $BeBq_2$, and a combination thereof, but is not limited thereto.

Either one of the charge auxiliary layers 40 and 50 may be omitted.

The organic photoelectronic device may be applied to various fields, for example a solar cell, an image sensor, a photo-detector, a photo-sensor, and an organic light emitting diode (OLED), but is not limited thereto.

Hereinafter, an example of an image sensor including the organic photoelectronic device is described referring to drawings. As an example of an image sensor, an organic CMOS image sensor is described.

Figure 3:
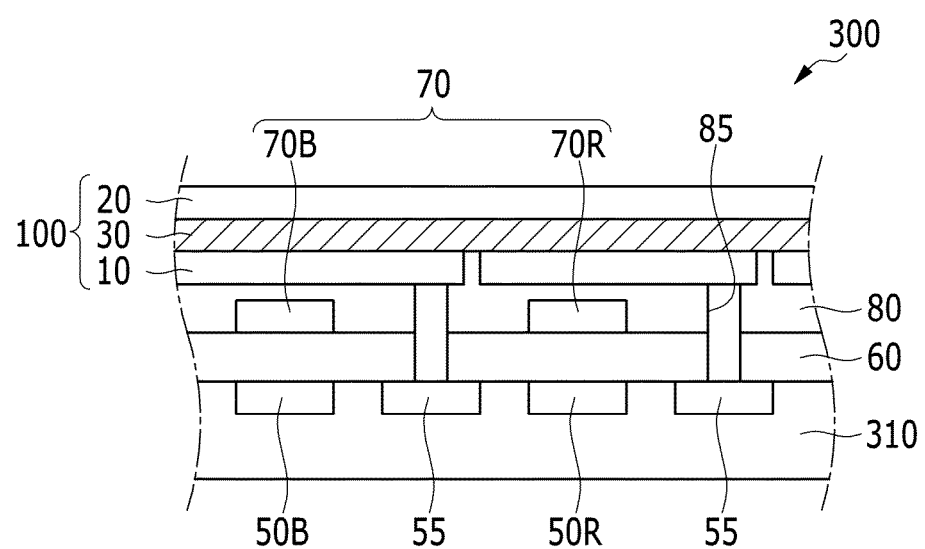
FIG. 3 is a cross-sectional view showing a CMOS image sensor according to example embodiments.

FIG. 3 is a cross-sectional view showing an organic CMOS image sensor according to example embodiments.

FIG. 3 illustrates blue, green, and red pixels that are adjacent to one another, but is not limited thereto.

Referring to FIG. 3, an organic CMOS image sensor 300 according to example embodiments includes a semiconductor substrate 310 integrated with photo-sensing devices 50B and 50R, a transmission transistor (not shown), and a charge storage 55, a lower insulation layer 60, a color filter 70, an upper insulation layer 80, and an organic photoelectronic device 100.

The semiconductor substrate 310 may be a silicon substrate, and is integrated with the photo-sensing device 50B and 50R, the transmission transistor (not shown), and the charge storage 55. The photo-sensing device 50 may be a photodiode.

The photo-sensing devices 50B and 50R, the transmission transistor, and/or the charge storage 55 may be integrated in each pixel, and as shown in the drawing, the photo-sensing devices 50B and 50R may be included in a blue pixel and a red pixel and the charge storage 55 may be included in a green pixel.

The photo-sensing devices 50B and 50R sense light, the information sensed by the photo-sensing devices may be transferred by the transmission transistor, the charge storage 55 is electrically connected with the organic photoelectronic device 100, and the information of the charge storage 55 may be transferred by the transmission transistor.

A metal wire (not shown) and a pad (not shown) are formed on the semiconductor substrate 310. In order to decrease signal delay, the metal wire and pad may be made of a metal having low resistivity, for example, aluminum (Al), copper (Cu), silver (Ag), and alloys thereof, but is not limited thereto. Further, it is not limited to the structure, and the metal wire and pad may be positioned under the photo-sensing devices 50B and 50R.

The lower insulation layer 60 is formed on the metal wire and the pad. The lower insulation layer 60 may be made of an inorganic insulating material such as a silicon oxide and/or a silicon nitride, or a low dielectric constant (low K) material such as SiC, SiCOH, SiCO, and SiOF. The lower insulation layer 60 has a trench exposing the charge storage 55. The trench may be filled with fillers.

A color filter 70 is formed on the lower insulation layer 60. The color filter 70 includes a blue filter 70B formed in the blue pixel and a red filter 70R filled in the red pixel. In example embodiments, a green filter is not included, but a green filter may be further included.

The upper insulation layer 80 is formed on the color filter 70. The upper insulation layer 80 may eliminate a step caused by the color filters 70 and smoothes the surface. The upper insulation layer 80 and lower insulation layer 60 may include a contact hole (not shown) exposing a pad, and a through-hole 85 exposing the charge storage 55 of the green pixel.

The organic photoelectronic device 100 is formed on the upper insulation layer 80. The organic photoelectronic device 100 includes the first electrode 10, the active layer 30, and the second electrode 120 as described above.

The first electrode 10 and the second electrode 20 may be transparent electrodes, and the active layer 30 selectively absorbs light in a green wavelength region as described above and may replace a color filter of a green pixel.

When light enters from the second electrode 20, the light in a green wavelength region may be mainly absorbed in the active layer 30 and photoelectrically converted, while the light in the rest of the wavelength regions passes through first electrode 10 and may be sensed in a photo-sensing device 50B and 50R.

Figure 4:
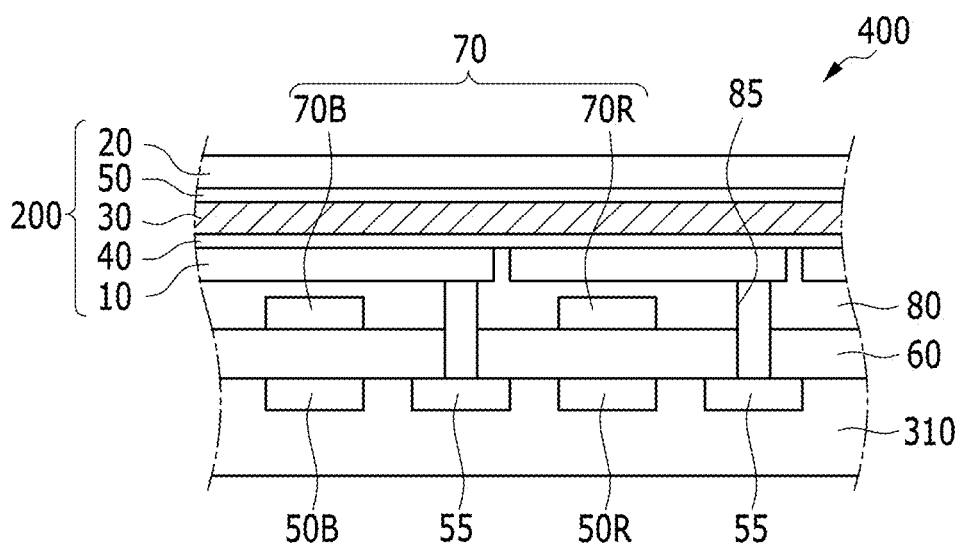
FIG. 4 is a cross-sectional view showing a CMOS image sensor according to example embodiments.

FIG. 4 is cross-sectional view showing an organic CMOS image sensor according to example embodiments.

Referring to FIG. 4, an organic CMOS image sensor 400 according to example embodiments includes a semiconductor substrate 310 integrated with photo-sensing devices 50B and 50R, a transmission transistor (not shown), and charge storage 55, a lower insulation layer 60, color filters 70B and 70R, an upper insulation layer 80, and an organic photoelectronic device 200, like the example embodiment illustrated in FIG. 3.

However, the organic photoelectronic device 200 further includes charge auxiliary layers 40 and 50. The charge auxiliary layers 40 and 50 are the same as above, and one of the charge auxiliary layers 40 and 50 may be omitted.

Hereinafter, the present disclosure is illustrated in more detail with reference to examples. However, these are examples, and the present disclosure is not limited thereto.

SYNTHESIS EXAMPLE

Synthesis Example 1

[Chemical Formula 1m]

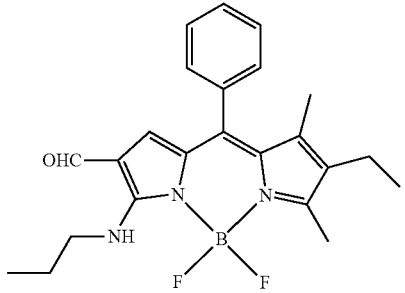

1.1 g of 2-chloro-5-benzoyl-pyrrole and 1.5 mL of $POCl_3$ are dissolved in 60 ml of $CH_2Cl_2$, and the solution is agitated at room temperature for 3 hours. Subsequently, 2.00 g of 2,4-dimethyl-3-ethylpyrrole is added to the solution, and the mixture is additionally agitated for 36 hours and then washed and dried. The obtained material is dissolved in toluene, a small amount of triethylamine is added thereto, and the mixture is agitated at room temperature for one hour. Subsequently, 1.8 mL of $BF_3OEt_2$ is added thereto, and the mixture is reacted at 100° C. for 10 hours. Subsequently, the resultant is washed and vacuum-dried. The obtained material is dissolved in 20 ml of acetonitrile, 170 μl of propane-1-amine is added thereto, and a material obtained by refluxing the mixture for 10 hours while the mixture is agitated is recrystallized, obtaining a powder-type compound represented by the above Chemical Formula 1 m.

MALD-TOF: 409.13 (M+), 409.21 (calculated) for $C_{23}H_{26}BF_2N_3O$, $^1$H NMR (CDCl, Bruker 500 MHz): δ 1.06 (t, 3H), 1.54 (s, 3H), 1.83 (t, 3H), 2.40 (q, 2H), 2.68 (s, 3H), 4.61 (d, 2H), 6.47 (s, 1H), 7.26-7.34 (m, 2H), 7.46-7.56 (m, 3H).

Synthesis Example 2

[Chemical Formula 1n]

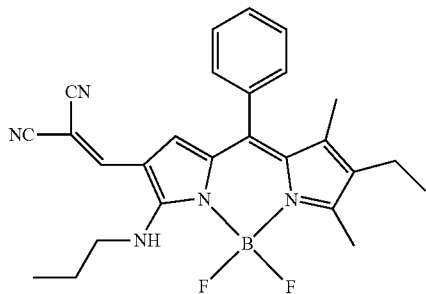

A compound represented by the above Chemical Formula 1n is obtained by dissolving the compound of Example 1 in ethanol, adding malononitrile and ammonium acetate thereto, and recrystallizing a product obtained from the mixture.

MALD-TOF: 458.03 (M+), 475.22 (calculated) for $C_{26}H_{26}BF_2N_5$, $^1$H NMR (CDCl, Bruker 500 MHz): δ 1.06 (t, 3H), 1.54 (s, 3H), 1.83 (t, 3H), 2.40 (q, 2H), 2.68 (s, 3H), 4.61 (d, 2H), 6.47 (s, 1H), 7.26-7.34 (m, 2H), 7.46-7.56 (m, 3H), 8.20 (s, 1H).

Synthesis Example 3

[Chemical Formula 1o]

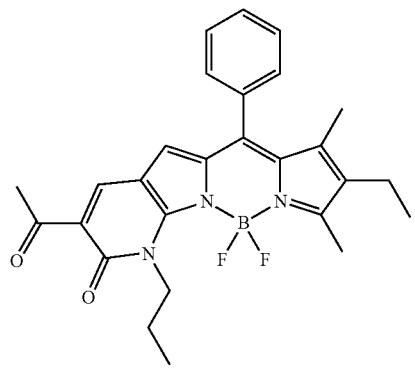

The compound of Synthesis Example 1 is dissolved in ethanol, and piperidine and ethylacetoacetate are added thereto. Subsequently, a product obtained therefrom is refluxed for 4 hours and then dried and recrystallized, obtaining a compound represented by the above Chemical Formula 1o.

MALD-TOF: 475.21 (M+), 475.22 (calculated) for $C_{27}H_{28}BF_2N_3O_2$, $^1$H NMR (CDCl, Bruker 500 MHz): δ 1.06 (t, 3H), 1.54 (s, 3H), 1.83 (t, 3H), 2.40 (q, 2H), 2.68 (s, 3H), 4.61 (d, 2H), 6.47 (s, 1H), 7.26-7.34 (m, 2H), 7.46-7.56 (m, 3H). 8.21 (s, 1H)

Synthesis Example 4

[Chemical Formula 1p]

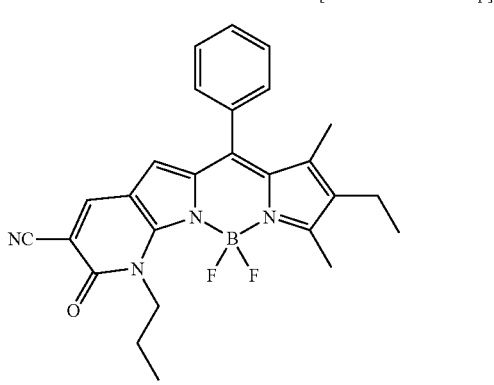

The compound of Synthesis Example 1 is dissolved in anhydrous ethanol, and piperidine and ethylcyanoacetate are added thereto. Subsequently, a product obtained therefrom is refluxed for 4 hours and then dried and recrystallized, obtaining a compound represented by the above Chemical Formula 1p.

MALD-TOF: 458.11 (M+), 458.21 (calculated) for $C_{26}H_{25}BF_2N_4O$, $^1$H NMR (CDCl, Bruker 500 MHz): δ 1.05 (t, 3H), 1.50 (s, 3H), 1.82 (t, 3H), 2.41 (q, 2H), 2.69 (s, 3H), 4.60 (d, 2H), 6.40 (s, 1H), 7.26-7.34 (m, 2H), 7.52-7.83 (m, 3H) 8.13 (s, 1H)

Synthesis Example 5

[Chemical Formula 1j]

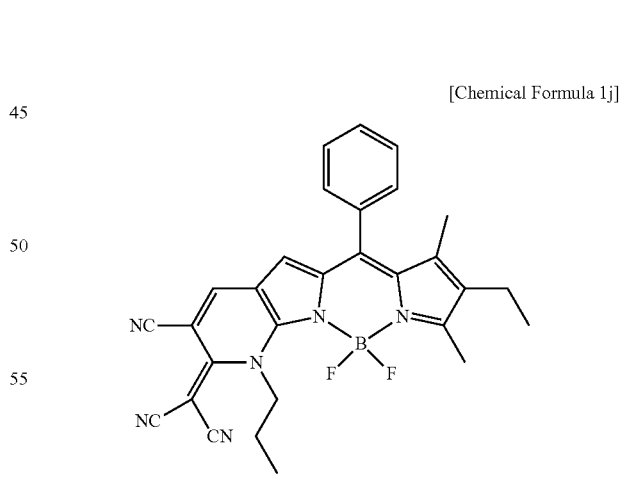

The compound of Synthesis Example 3 is dissolved in ethanol, malononitrile and ammonium acetate are added thereto, and a product obtained therefrom is recrystallized, obtaining a compound represented by the above Chemical Formula 1j.

MALD-TOF: 507.47 (M+), 506.22 (calculated) for $C_{27}H_{28}BF_2N_3O_2$, $^1$H NMR (CDCl, Bruker 500 MHz): δ 1.05 (t, 3H), 1.50 (s, 3H), 1.82 (t, 3H), 2.41 (q, 2H), 2.69 (s, 3H), 4.60 (d, 2H), 6.40 (s, 1H), 7.26-7.34 (m, 2H), 7.52-7.83 (m, 3H), 7.89 (s, 1H).

Evaluation 1: Absorbance Characteristics

Absorbance characteristics of the compounds according to Synthesis Examples 1 to 5 are evaluated depending on a wavelength.

The absorbance characteristics are evaluated by thermally depositing each compound according to Synthesis Examples 1 to 5 at a speed of 0.1 to 1.0 Å/s under relatively high vacuum (<10$^{-7}$ Torr) to respectively form 50 nm to 100 nm-thick thin films and radiating ultraviolet-visible ray (UV-Vis) to the films by using a Cary 5000 UV spectroscope (Varian Inc.).

The results are provided in Table 1.

Referring to Table 1, the compounds of Synthesis Examples 1 to 5 are found to have a maximum absorbance wavelength ($\lambda_{max}$) in a range of about 500 nm to 600 nm and to selectively absorb light in a green wavelength region.

TABLE 1

| | Maximum absorption wavelength (λmax, nm) | FWHM (nm) |
|---|---|---|
| Synthesis Example 1 | 573 | 87 |
| Synthesis Example 2 | 595 | 115 |
| Synthesis Example 3 | 582 | 109 |
| Synthesis Example 4 | 563 | 107 |
| Synthesis Example 5 | 577 | 96 |

Evaluation 2: Thin Film Characteristics

Thin film characteristics of the compound according to Synthesis Example 3 are evaluated.

Surface characteristics are evaluated by thermally depositing the compound of Synthesis Example 3 at a speed of 0.5 to 1.0 Å/s under relatively high vacuum (<10$^{-7}$ Torr) to form a 50 to 100 nm-thick film and using an atomic force microscope (Dimension V, Veeco Co.).

Figure 5:
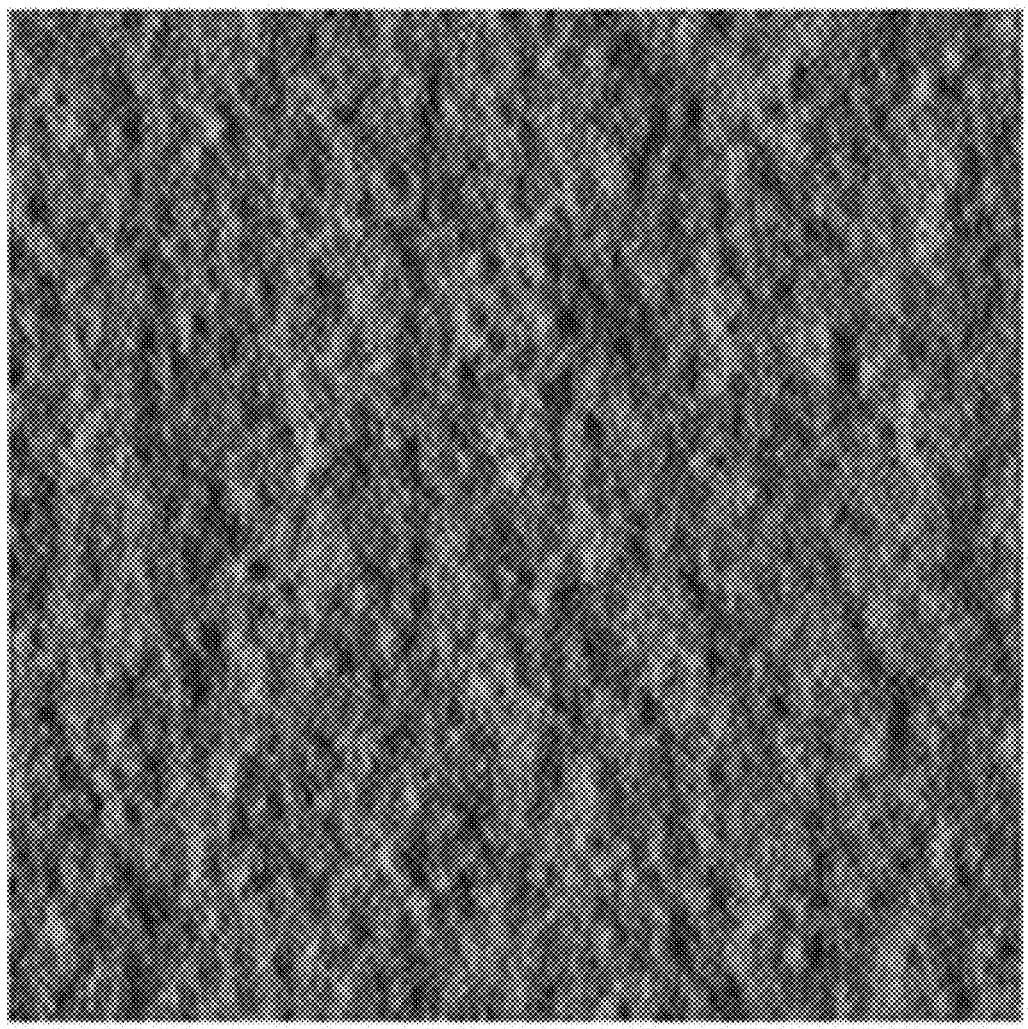
FIG. 5 is a photograph showing thin film characteristics of a compound according to Synthesis Example 3.
Figure 6:
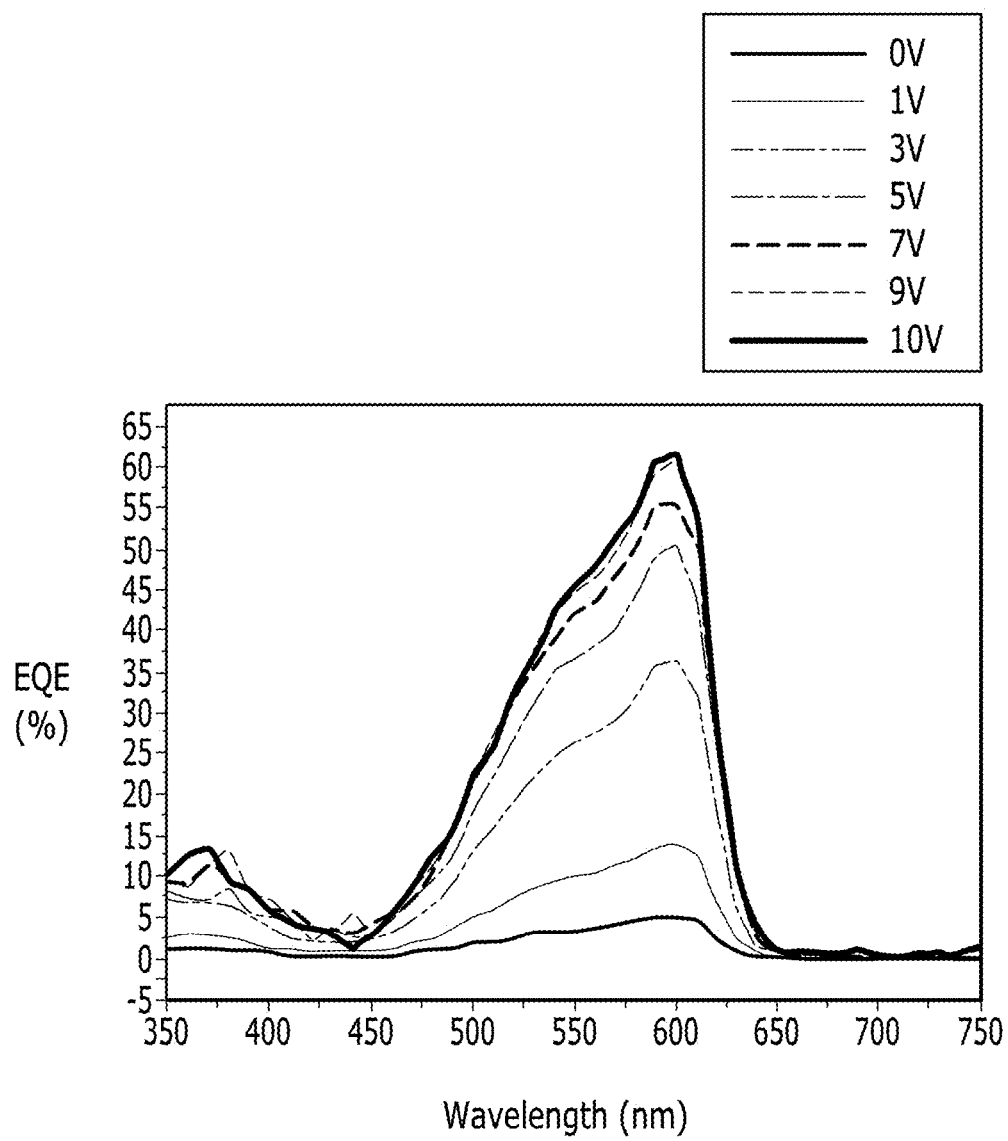
FIG. 6 to FIG. 11 are graphs respectively showing external quantum efficiency (EQE) of each organic photoelectronic device according to Examples 1 to 6 depending on a wavelength and a voltage.
Figure 7:
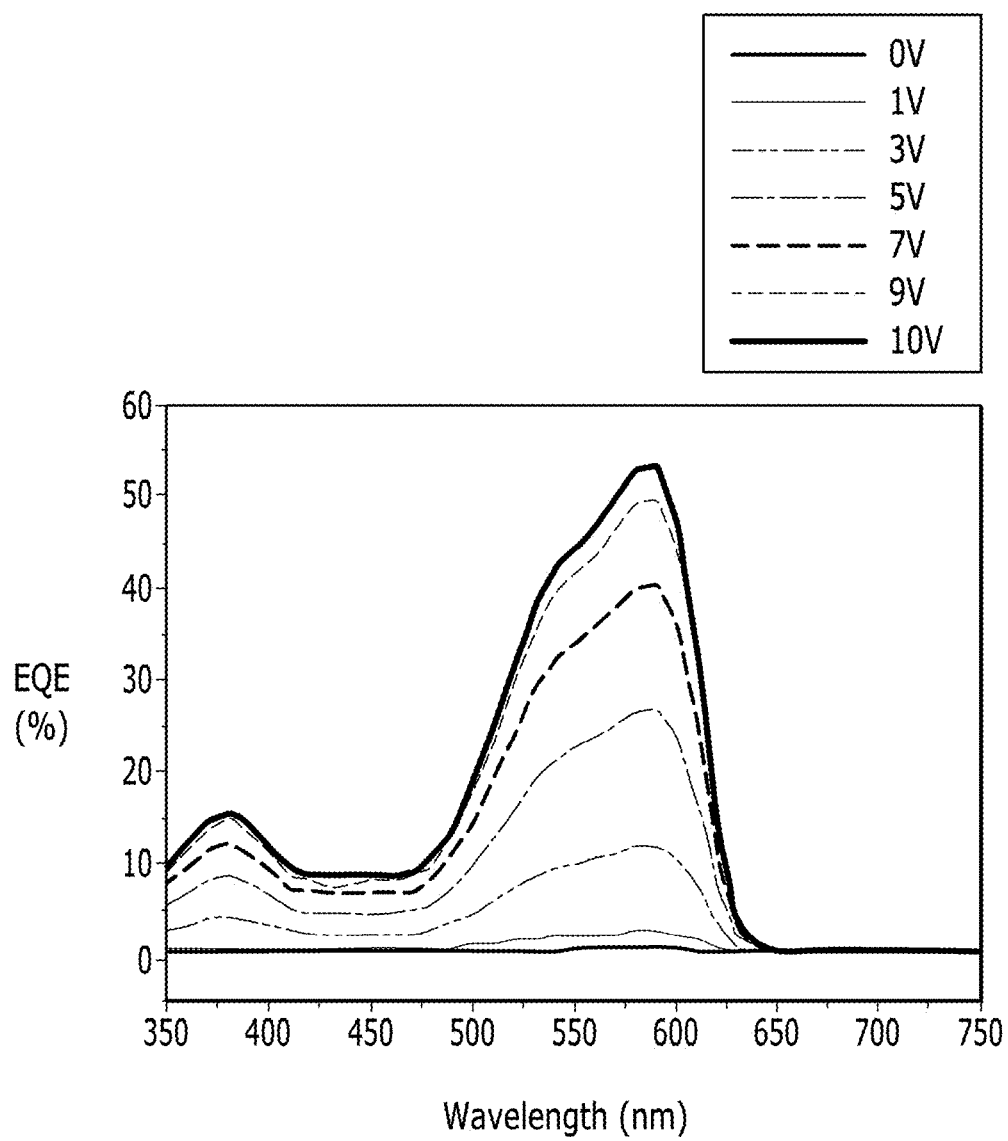
Figure 8:
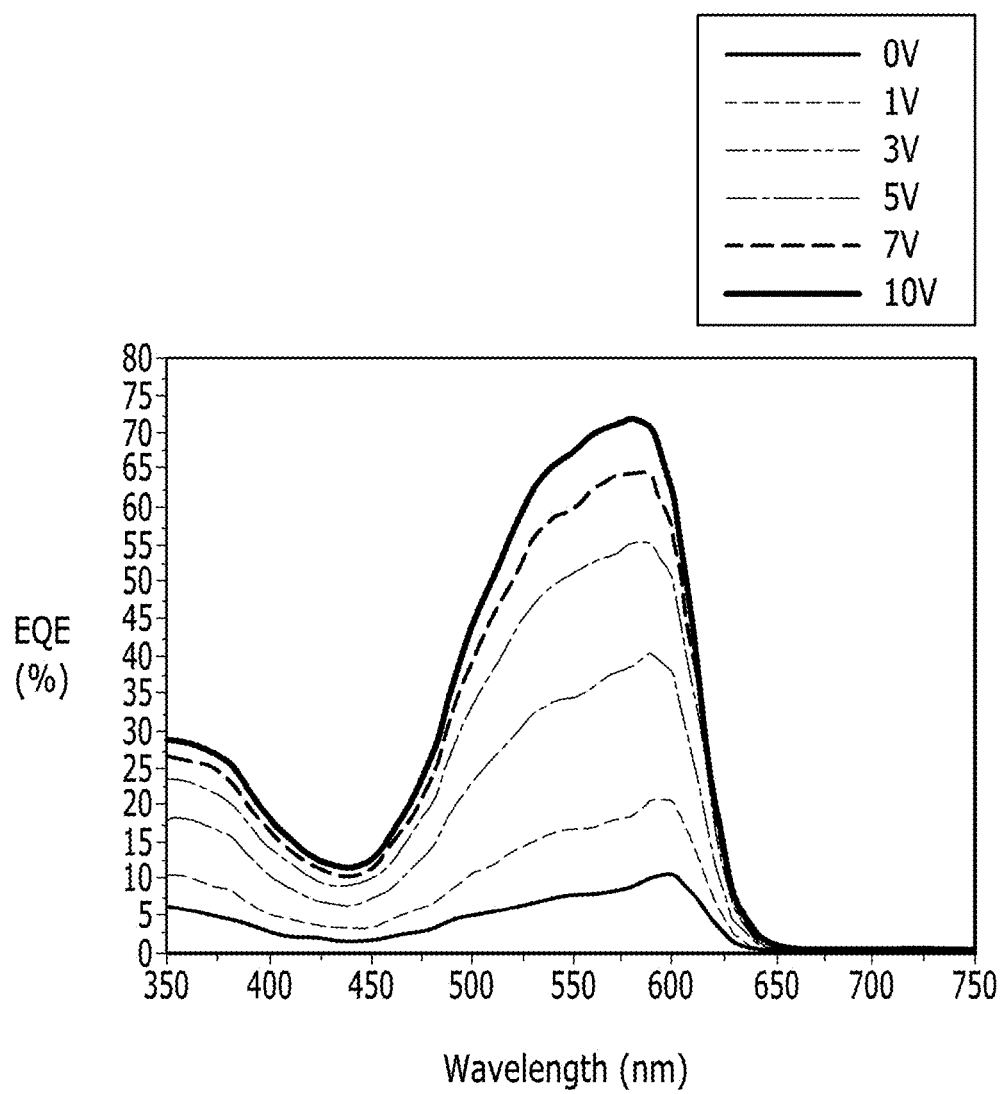
Figure 9:
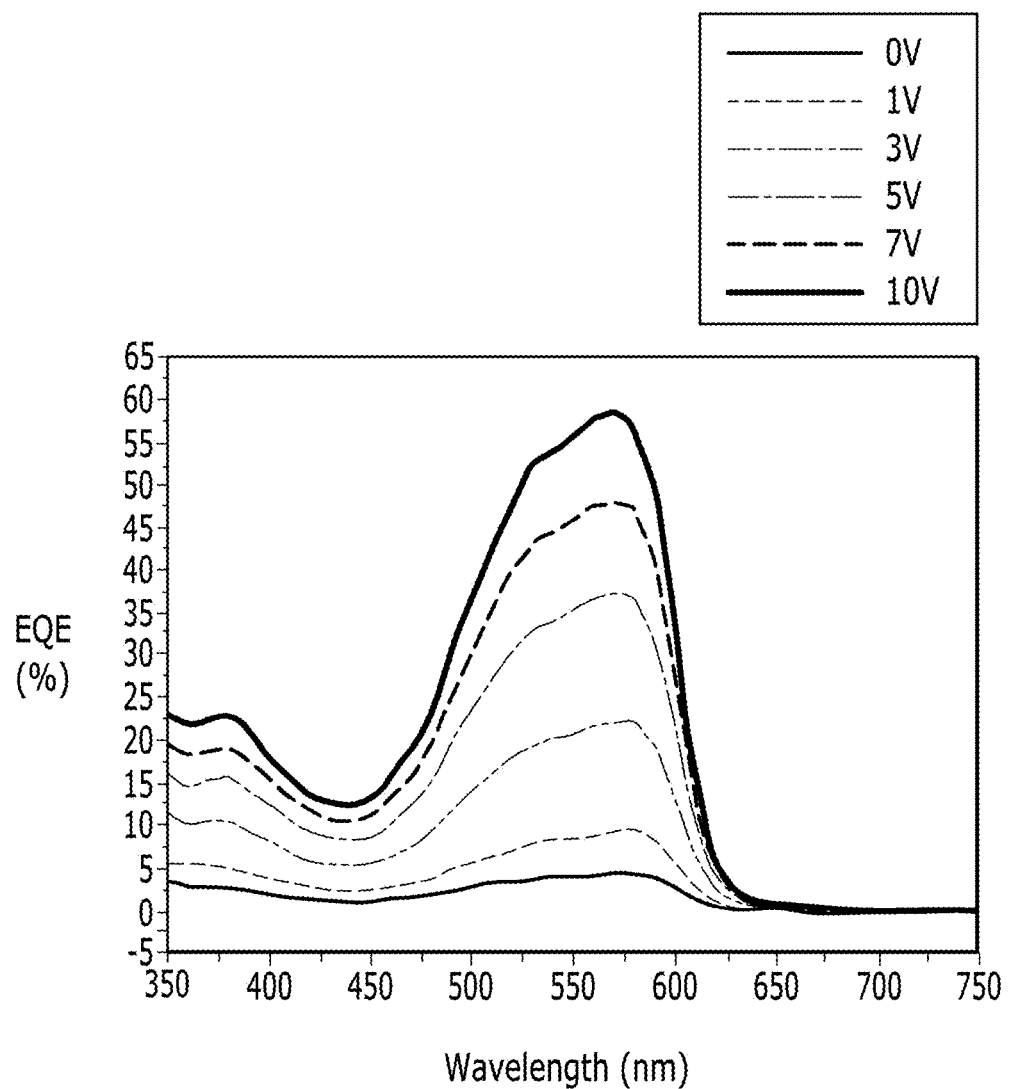
Figure 10:
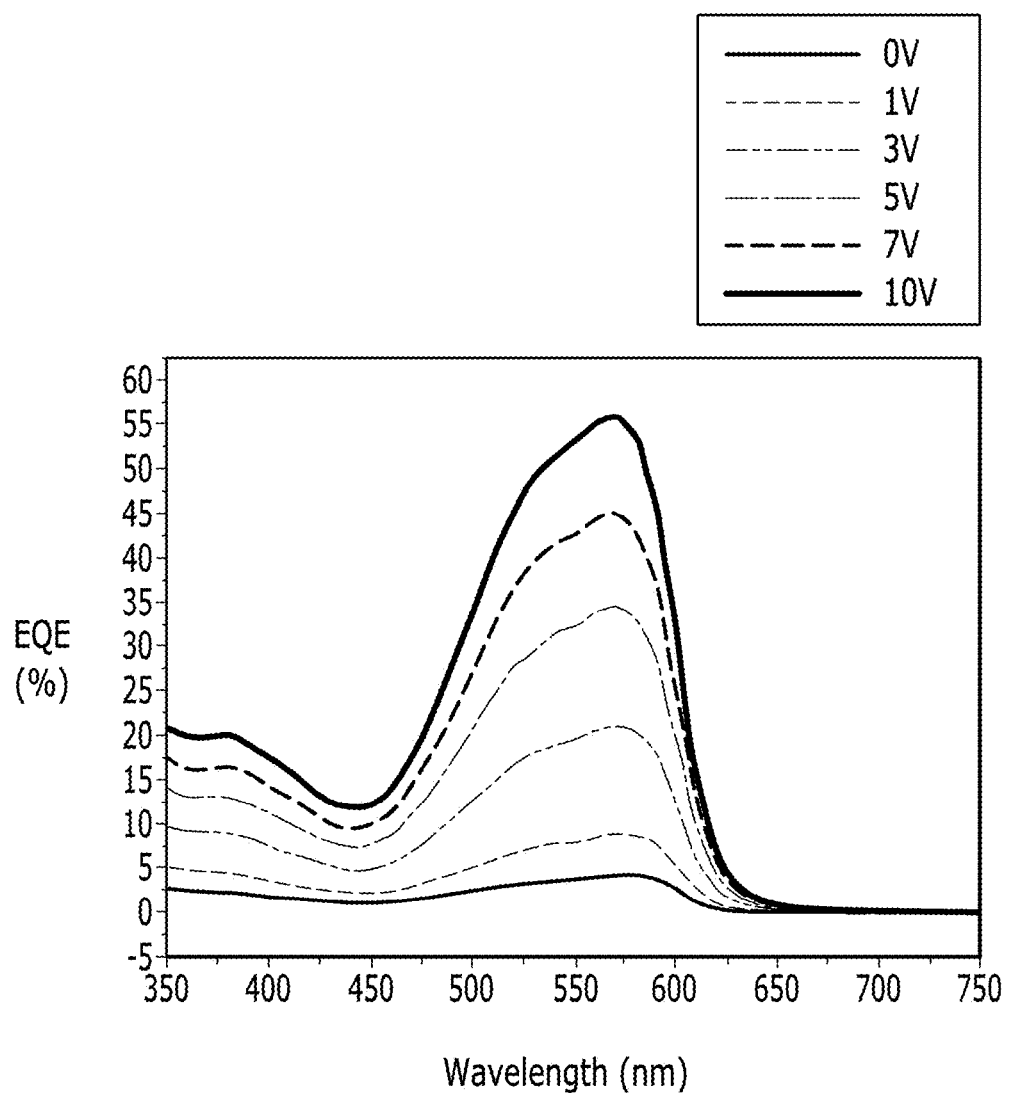
Figure 11:
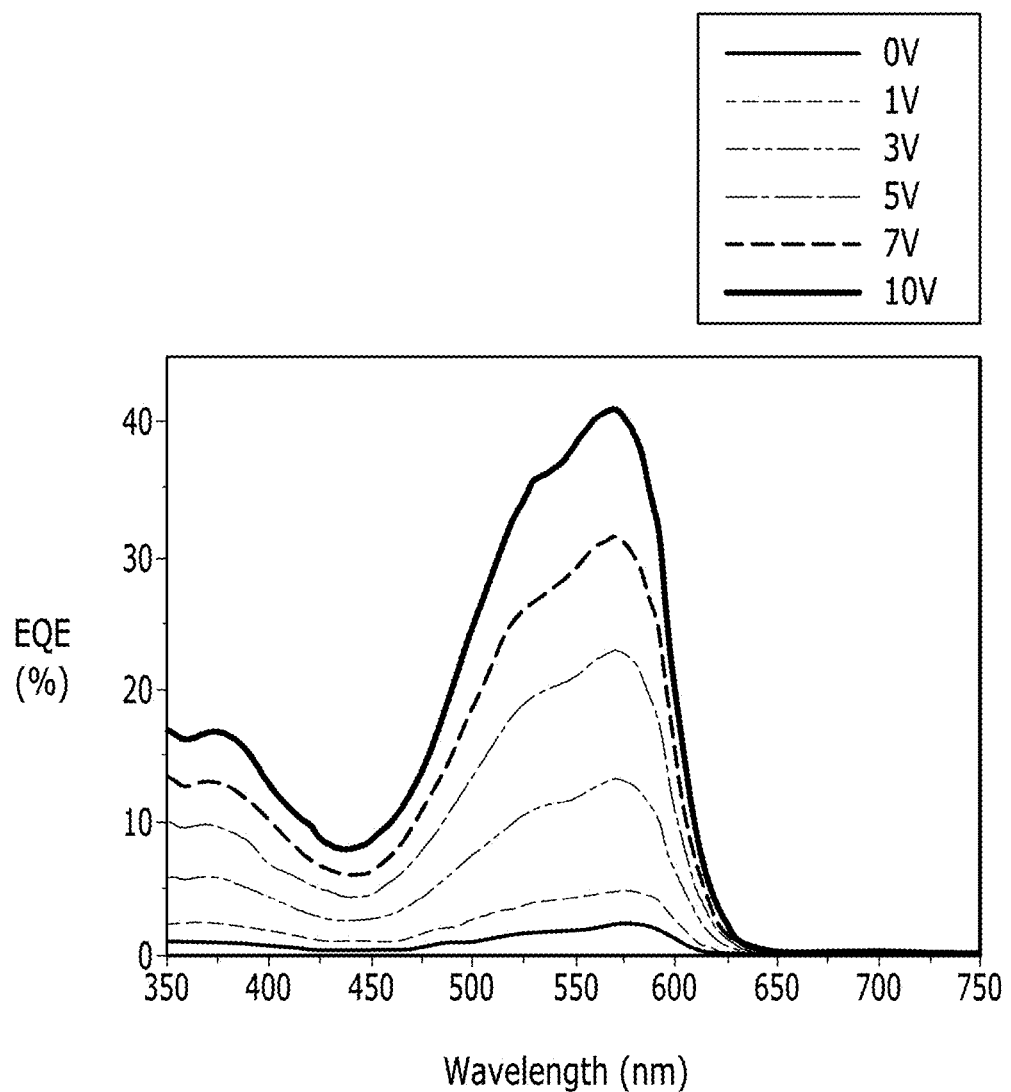

FIG. 5 is a photograph showing the thin film characteristics of the compound according to Synthesis Example 3. Referring to FIG. 5, the thin film formed of the compound according to Synthesis Example 3 is found to have a uniform surface and improved thin film characteristics.

Evaluation 3: Energy Level

Energy level of the compounds represented by the following Chemical Formulas 1a to 1p is evaluated.

The energy level is calculated as a B3LYP/6-31G basis set in a density functional theory (DFT) method by using Gaussian software and evaluated with an AC-2 photoelectron spectrometer (Hitachi Co.).

[Chemical Formula 1a]

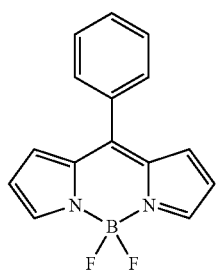

[Chemical Formula 1b]

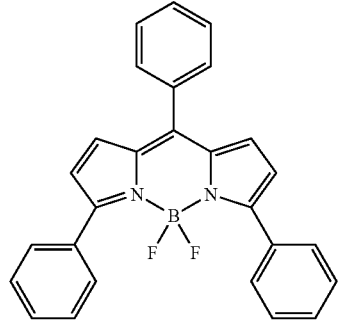

[Chemical Formula 1c]

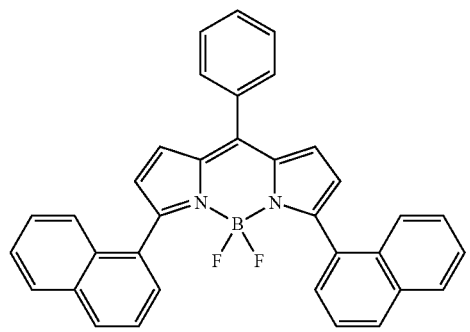

[Chemical Formula 1d]

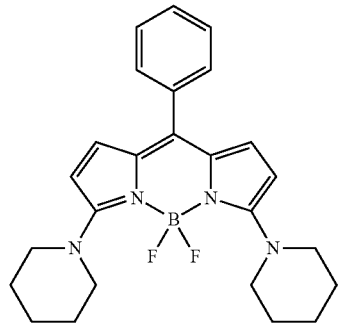

[Chemical Formula 1e]

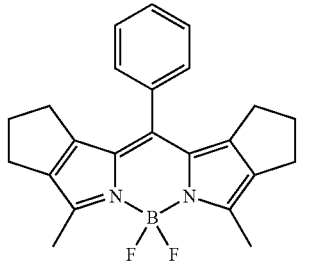

[Chemical Formula 1f]

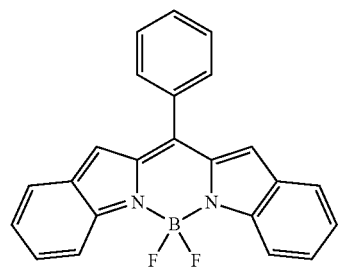

[Chemical Formula 1g]
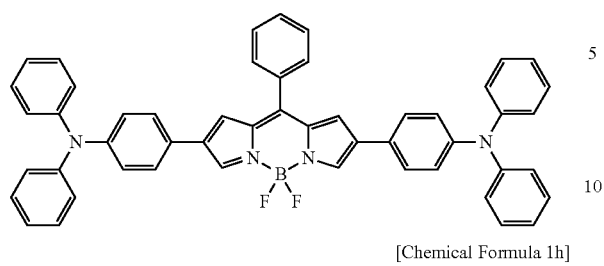
[Chemical Formula 1h]
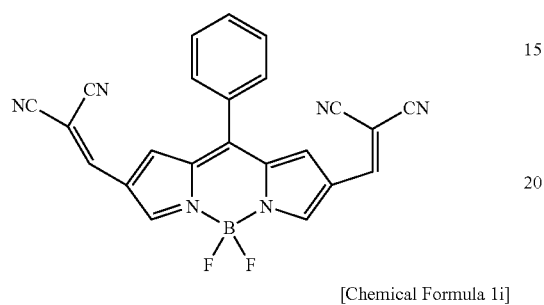
[Chemical Formula 1i]
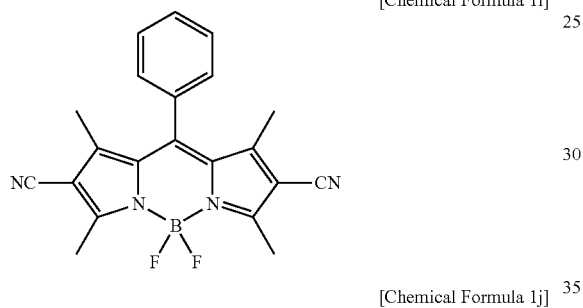
[Chemical Formula 1j]
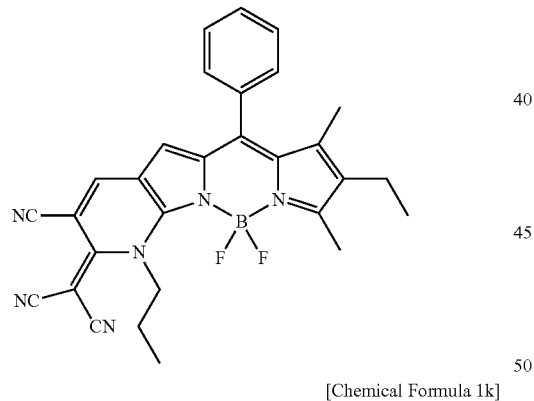
[Chemical Formula 1k]
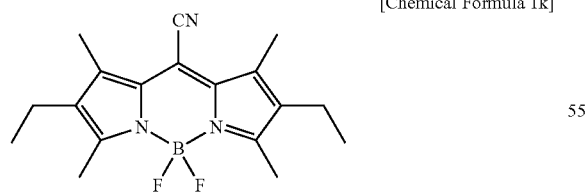
[Chemical Formula 1l]
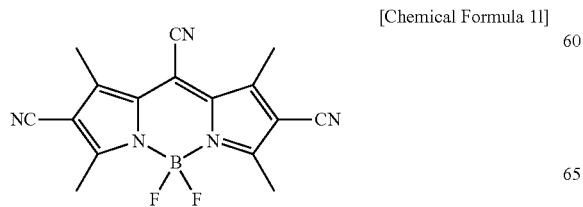
[Chemical Formula 1m]
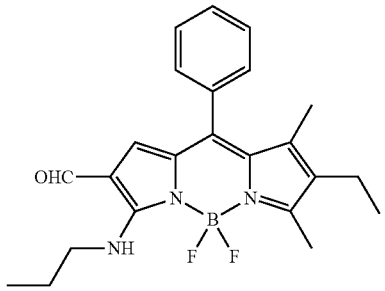
[Chemical Formula 1n]
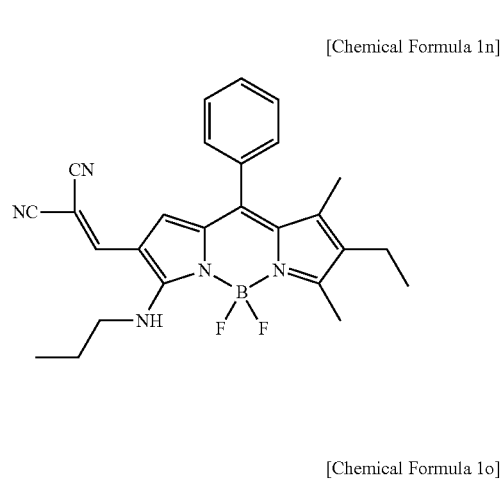
[Chemical Formula 1o]
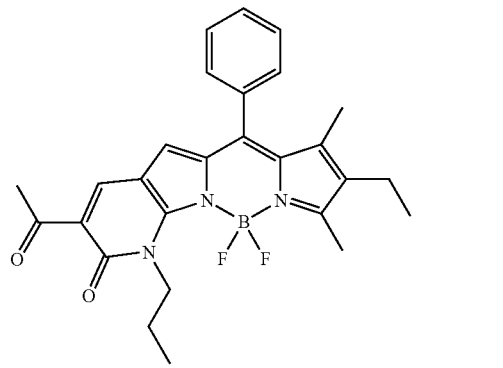
[Chemical Formula 1p]
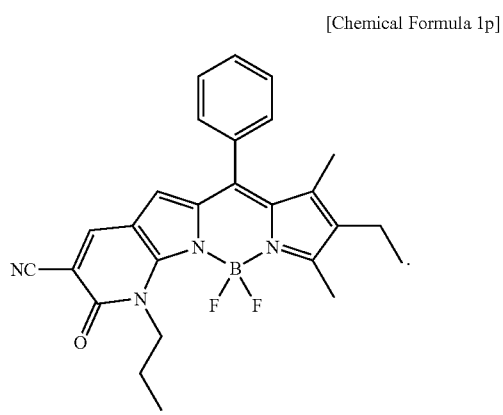

The results are provided in Table 2.

TABLE 2

|  | HOMO (eV) | LUMO (eV) | Bandgap (Eg., eV) |
| --- | --- | --- | --- |
| Chemical Formula 1a | −5.881 | −2.799 | 3.082 |
| Chemical Formula 1b | −5.343 | −2.702 | 2.641 |
| Chemical Formula 1c | −5.218 | −2.703 | 2.515 |
| Chemical Formula 1d | −4.404 | −1.921 | 2.483 |
| Chemical Formula 1e | −5.232 | −2.292 | 2.94 |
| Chemical Formula 1f | −5.677 | −3.279 | 2.398 |
| Chemical Formula 1g | −4.828 | −2.780 | 2.048 |
| Chemical Formula 1h | −6.850 | −4.119 | 2.731 |
| Chemical Formula 1i | −6.282 | −3.300 | 2.982 |
| Chemical Formula 1j | −5.646 | −3.489 | 2.157 |
| Chemical Formula 1k | −5.597 | −3.042 | 2.555 |
| Chemical Formula 1l | −6.733 | −4.112 | 2.621 |
| Chemical Formula 1m | −5.132 | −2.492 | 2.640 |
| Chemical Formula 1n | −5.404 | −2.940 | 2.464 |
| Chemical Formula 1o | −5.632 | −3.025 | 2.607 |
| Chemical Formula 1p | −5.644 | −3.070 | 2.574 |

Referring to Table 2, the compounds represented by Chemical Formulas 1a to 1p are found to have a HOMO level of about 4.3 to about 7.0 eV and an energy bandgap of about 1.9 to about 3.1 eV.

Manufacture of Organic Photoelectronic Device

Example 1

ITO is sputtered on a glass substrate to form an about 100 nm-thick anode, and molybdenum oxide (MoOx) is deposited to form a 30 nm-thick charge auxiliary layer thereon. Subsequently, the compound according to Synthesis Example 3 (an n-type semiconductor) and a compound represented by the following Chemical Formula 3a (a p-type semiconductor) in a thickness ratio of 1:1 are co-deposited to form a 70 nm-thick active layer on the molybdenum oxide (MoOx) thin layer. Subsequently, aluminum (Al) is sputtered on the active layer to form an 80 nm-thick cathode, manufacturing an organic photoelectronic device.

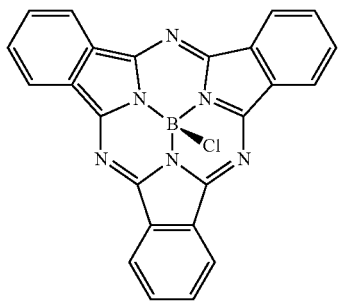

[Chemical Formula 3a]

Example 2

An organic photoelectronic device is manufactured according to the same method as Example 1, except for using a compound represented by the following Chemical Formula 4 (an n-type semiconductor) and the compound according to Synthesis Example 4 (a p-type semiconductor) instead of the compound according to Synthesis Example 3 (an n-type semiconductor) and the compound represented by the above Chemical Formula 3a (a p-type semiconductor).

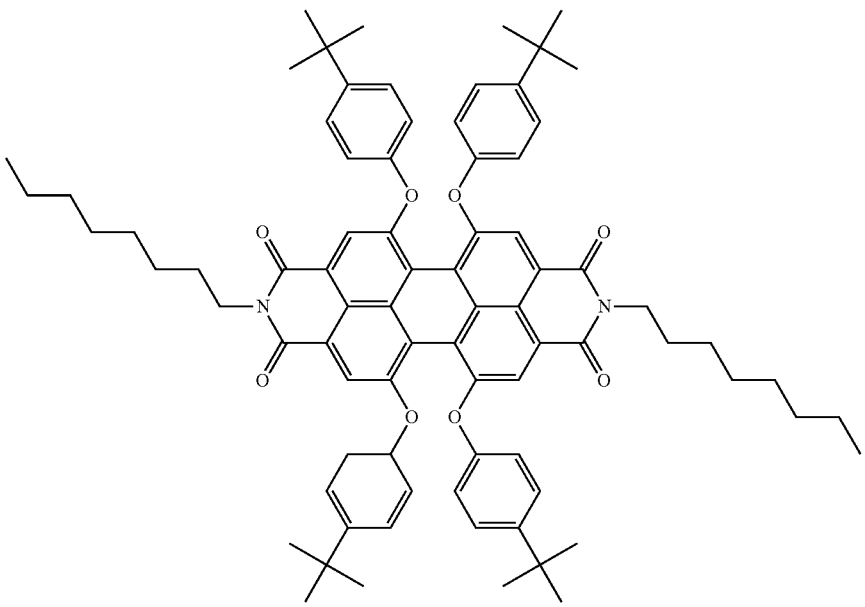

[Chemical Formula 4]

Example 3

An organic photoelectronic device is manufactured according to the same method as Example 1, except for using the compound according to Synthesis Example 4 (an n-type semiconductor) and a compound represented by the following Chemical Formula 3a (a p-type semiconductor) instead of the compound according to Synthesis Example 3 (an n-type semiconductor) and the compound represented by the above Chemical Formula 3a (a p-type semiconductor).

Example 4

An organic photoelectronic device is manufactured according to the same method as Example 1, except for using the compound according to Synthesis Example 4 (an n-type semiconductor) and a compound represented by the following Chemical Formula 2a (a p-type semiconductor) instead of the compound according to Synthesis Example 3 (an n-type semiconductor) and the compound represented by the above Chemical Formula 3a (a p-type semiconductor).

[Chemical Formula 2a]

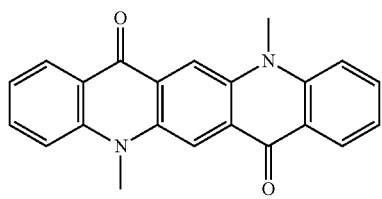

Example 5

An organic photoelectronic device is manufactured according to the same method as Example 1, except for using the compound according to Synthesis Example 4 (an n-type semiconductor) and a compound represented by the following Chemical Formula 2b (a p-type semiconductor) instead of the compound according to Synthesis Example 3 (an n-type semiconductor) and the compound represented by the above Chemical Formula 3a (a p-type semiconductor).

[Chemical Formula 2b]

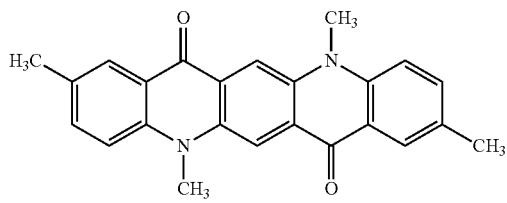

Example 6

An organic photoelectronic device is manufactured according to the same method as Example 1, except for using the compound according to Synthesis Example 4 (an n-type semiconductor) and a compound represented by the following Chemical Formula 2d (a p-type semiconductor) instead of the compound according to Synthesis Example 3 (an n-type semiconductor) and the compound represented by the above Chemical Formula 3a (a p-type semiconductor).

[Chemical Formula 2d]

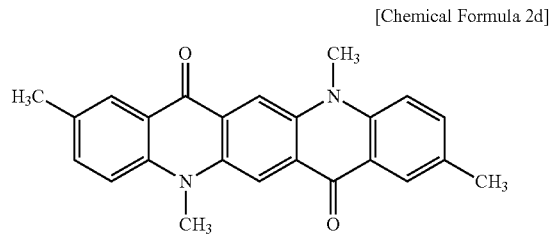

Evaluation 4: External Quantum Efficiency (EQE)

External quantum efficiency (EQE) of the organic photoelectronic devices according to Examples 1 to 6 is evaluated depending on a wavelength and a voltage.

The external quantum efficiency is measured by using an IPCE measurement system (McScience Co. Ltd., Korea). First of all, the IPCE measurement system is calibrated by using a Si photodiode (Hamamatsu Photonics K.K., Japan) and mounted on the organic photoelectronic devices according to Examples 1 to 6, and their external quantum efficiency is measured in a wavelength range of about 350 to 750 nm.

FIGS. 6 to 11 are graphs respectively showing the external quantum efficiency (EQE) of the organic photoelectronic devices according to Examples 1 to 6 depending on a wavelength and a voltage.

Referring to FIGS. 6 to 11, the organic photoelectronic devices according to Examples 1 to 6 show satisfactory external quantum efficiency (EQE) in a green wavelength region of about 500 nm to 600 nm.

Evaluation 5: Thermal Stability

Thermal stability of the organic photoelectronic devices according to Examples 4 and 5 is evaluated.

The thermal stability is evaluated by measuring current density change of the organic photoelectronic devices according to Examples 4 and 5 after being allowed to stand at 120° C. for 30 minutes.

Figure 12:
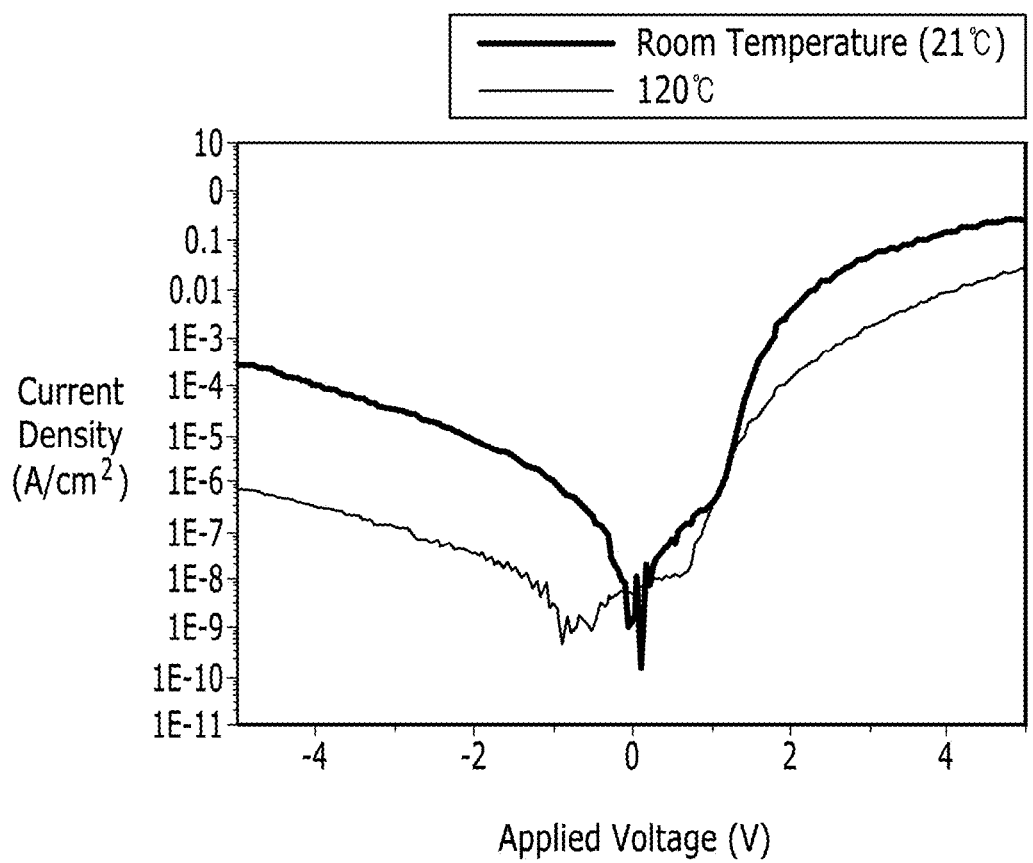
FIG. 12 is a graph showing current density change of the organic photoelectronic device according to Example 4 when allowed to stand at 120° C. for 30 minutes.
Figure 13:
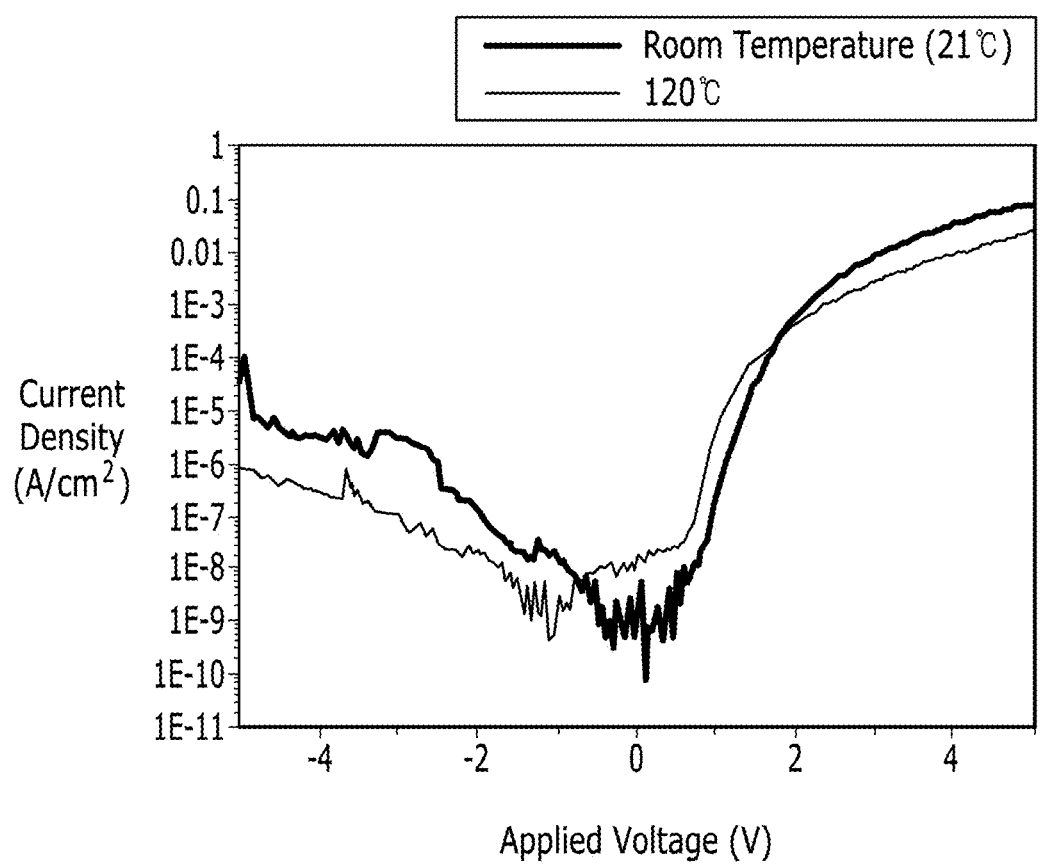
FIG. 13 is a graph showing current density change of the organic photoelectronic device according to Example 5 when allowed to stand at 120° C. for 30 minutes.

FIG. 12 is a graph showing current density change of the organic photoelectronic device according to Example 4 from room temperature (21° C.) after being allowed to stand at 120° C. for 30 minutes, and FIG. 13 is a graph showing current density change of the organic photoelectronic device according to Example 5 from room temperature (21° C.) after being allowed to stand at 120° C. for 30 minutes.

Referring to FIGS. 12 and 13, the organic photoelectronic devices according to Examples 4 and 5 show that a dark current decreases after the organic photoelectronic devices are allowed to stand at 120° C. for 30 minutes, and thus, characteristics of the organic photoelectronic devices are found to be stabilized. Accordingly, the organic photoelectronic devices according to Examples 4 and 5 show relatively high thermal stability without deteriorating performance when being allowed to stand at a relatively high temperature.

While this disclosure has been described in connection with what is presently considered to be practical example embodiments, it is to be understood that the present disclosure is not limited to the disclosed embodiments, but, on the contrary, is intended to cover various modifications and equivalent arrangements included within the spirit and scope of the appended claims.

What is claimed is:

1. A compound represented by one of the following Chemical Formulae 1d to 1n:

[Chemical Formula 1d]

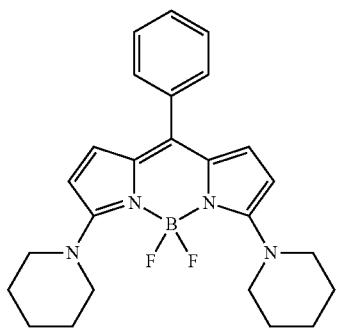

[Chemical Formula 1e]

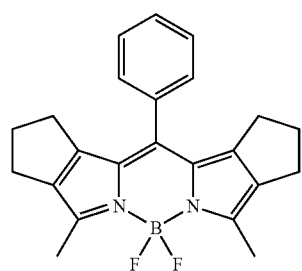

[Chemical Formula 1f]

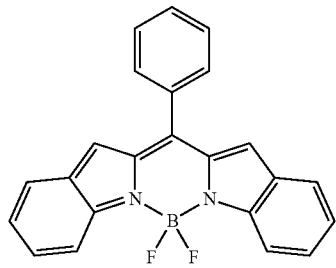

[Chemical Formula 1g]

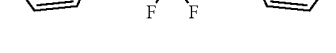

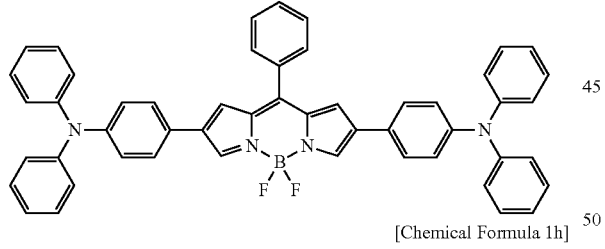

[Chemical Formula 1j]

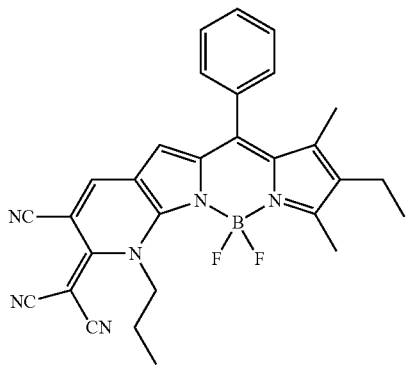

[Chemical Formula 1l]

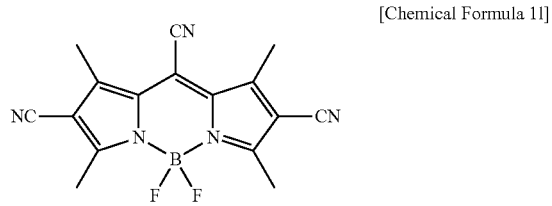

[Chemical Formula 1n]

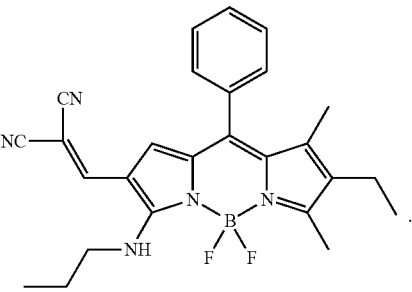

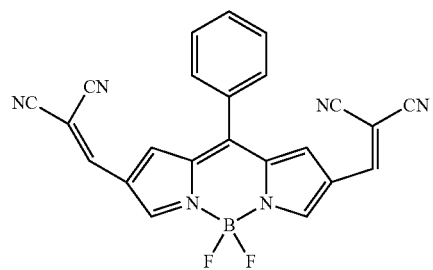

2. A thin film comprising the compound of claim 1.

3. The thin film of claim 2, wherein the thin film shows an absorbance curve having a full width at half maximum (FWHM) of about 50 nm to about 150 nm.

* * * * *